US011940406B2

(12) United States Patent
Sekiya et al.

(10) Patent No.: US 11,940,406 B2
(45) Date of Patent: *Mar. 26, 2024

(54) SENSOR ELEMENT AND GAS SENSOR

(71) Applicant: NGK INSULATORS, LTD., Aichi (JP)

(72) Inventors: Takayuki Sekiya, Nagoya (JP); Yusuke Watanabe, Nisshin (JP)

(73) Assignee: NGK INSULATORS, LTD., Nagoya (JP)

( * ) Notice: Subject to any disclaimer, the term of this patent is extended or adjusted under 35 U.S.C. 154(b) by 278 days.

This patent is subject to a terminal disclaimer.

(21) Appl. No.: 17/205,617

(22) Filed: Mar. 18, 2021

(65) Prior Publication Data

US 2021/0302355 A1    Sep. 30, 2021

(30) Foreign Application Priority Data

Mar. 30, 2020    (JP) .................................. 2020-060781
Mar. 15, 2021    (JP) .................................. 2021-041459

(51) Int. Cl.
*G01N 27/407*    (2006.01)
*G01N 27/409*    (2006.01)
(Continued)

(52) U.S. Cl.
CPC ....... *G01N 27/409* (2013.01); *G01N 27/4072* (2013.01); *G01N 27/41* (2013.01); *G01N 27/419* (2013.01); *G01N 33/0037* (2013.01)

(58) Field of Classification Search
CPC .. G01N 27/4075; G01N 27/409; G01N 27/41; G01N 27/419; G01N 27/407–4072; G01N 27/48
See application file for complete search history.

(56) References Cited

U.S. PATENT DOCUMENTS

2010/0243447 A1    9/2010  Fujisaki et al.
2015/0276659 A1*  10/2015  Sekiya ................. G01N 27/409
                                                                      204/416
2016/0061768 A1*   3/2016  Nakasone ............ G01N 27/301
                                                                      204/412

FOREIGN PATENT DOCUMENTS

JP           5323752 B2    10/2013

* cited by examiner

*Primary Examiner* — Joshua L Allen
*Assistant Examiner* — Vivian A Tran
(74) *Attorney, Agent, or Firm* — MATTINGLY & MALUR, PC

(57) ABSTRACT

A sensor element includes an element body having a measurement-object gas flow section being provided therein, a first measurement pump cell that includes a first measurement electrode being disposed in a first measurement chamber and a first outer measurement electrode and that pumps out oxygen produced in a first measurement chamber, and a second measurement pump cell that includes a second measurement electrode being disposed in a second measurement chamber and a second outer measurement electrode and that pumps out oxygen produced in a second measurement chamber. The measurement-object gas flow section is configured such that a measurement-object gas passes through an oxygen concentration adjustment chamber and a first measurement-electrode diffusion-rate-controlling section in this order and reaches the first measurement chamber and that the measurement-object gas passes through the first measurement chamber and a second measurement-electrode diffusion-rate-controlling section in this order and reaches the second measurement chamber.

6 Claims, 9 Drawing Sheets

(51) Int. Cl.
*G01N 27/41* (2006.01)
*G01N 27/419* (2006.01)
*G01N 33/00* (2006.01)

SENSOR ELEMENT AND GAS SENSOR

The application claims the benefit of Japanese Patent Application No. 2020-060781 filed Mar. 30, 2020, and Japanese Patent Application No. 2021-041459 filed Mar. 15, 2021, which are hereby incorporated by reference herein in its entirety.

BACKGROUND OF THE INVENTION

1. Field of the Invention

The present invention relates to a sensor element and a gas sensor.

2. Description of the Related Art

In the related art, limiting-current gas sensors are known that detect the concentration of a specific gas, such as NOx, in a measurement-object gas, such as exhaust gas of an automobile. For example, PTL 1 describes a gas sensor including a layered body, a pump electrode, and a measurement electrode. The layered body is formed of a plurality of oxygen-ion-conductive solid electrolyte layers, the pump electrode constitutes an electrochemical pump cell for adjusting an oxygen partial pressure of an internal cavity of the layered body, and the measurement electrode is disposed inside the layered body. To detect the NOx concentration by using this gas sensor, first, the oxygen concentration in the measurement-object gas in the internal cavity is adjusted by using the pump electrode. Next, NOx in the measurement-object gas, which has been subjected to adjustment of the oxygen concentration, is reduced around the measurement electrode. Then, based on a pump current Ip2 that flows when oxygen around the measurement electrode is pumped out, the NOx concentration in the measurement-object gas is detected.

CITATION LIST

Patent Literature

[PTL 1] Japanese Patent No. 5323752

SUMMARY OF THE INVENTION

However, a single gas sensor can accurately measure the NOx concentration only in a limited range. For example, if the NOx concentration in the measurement-object gas is too high, the pump current Ip2 does not reach the limiting current, and the NOx concentration cannot be measured currently. In addition, if the NOx concentration in the measurement-object gas is too low, since the pump current Ip2 is too low, the measurement accuracy decreases by being influenced by errors or the like. Thus, a gas sensor that can measure the NOx concentration in a broader range has been desired.

The present invention has been made in order to solve such a problem, and a primary objective thereof is to accurately detect a specific gas concentration in a broad range.

To achieve the above primary objective, the present invention has employed the following configurations.

A first sensor element according to the present invention is a sensor element for detecting a concentration of a specific gas in a measurement-object gas, the sensor element including:

an element body including an oxygen-ion-conductive solid electrolyte layer and having a measurement-object gas flow section provided therein, the measurement-object gas flow section introducing the measurement-object gas and causing the measurement-object gas to flow;

an adjustment pump cell that adjusts an oxygen concentration in an oxygen concentration adjustment chamber in the measurement-object gas flow section;

a first measurement pump cell that includes a first measurement electrode and a first outer measurement electrode and that pumps out oxygen produced in a first measurement chamber from the specific gas, the first measurement electrode being disposed in the first measurement chamber provided on a downstream side of the oxygen concentration adjustment chamber in the measurement-object-gas flow section, the first outer measurement electrode being provided outside the element body so as to contact with the measurement-object gas; and a second measurement pump cell that includes a second measurement electrode and a second outer measurement electrode and that pumps out oxygen produced in a second measurement chamber from the specific gas, the second measurement electrode being disposed in the second measurement chamber provided on a downstream side of the oxygen concentration adjustment chamber in the measurement-object-gas flow section, the second outer measurement electrode being provided outside the element body so as to contact with the measurement-object gas, in which the measurement-object gas flow section is configured such that the measurement-object gas passes through the oxygen concentration adjustment chamber and a first measurement-electrode diffusion-rate-controlling section in this order and reaches the first measurement chamber and that the measurement-object gas passes through the first measurement chamber and a second measurement-electrode diffusion-rate-controlling section in this order and reaches the second measurement chamber.

In the first sensor element, the measurement-object gas flow section is configured such that the measurement-object gas passes through the oxygen concentration adjustment chamber and the first measurement-electrode diffusion-rate-controlling section in this order and reaches the first measurement chamber and that the measurement-object gas passes through the first measurement chamber and the second measurement-electrode diffusion-rate-controlling section in this order and reaches the second measurement chamber. In other words, the first measurement-electrode diffusion-rate-controlling section and the second measurement-electrode diffusion-rate-controlling section are disposed in series. Thus, the first sensor element is configured such that a second diffusion resistance $R_2$, which is a diffusion resistance of a route of the measurement-object gas from the outside of the sensor element to the second measurement electrode, is higher than a first diffusion resistance Ru which is a diffusion resistance of a route of the measurement-object gas from the outside of the sensor element to the first measurement electrode. Thus, even if the concentration of the specific gas in the measurement-object gas is higher in the second measurement pump cell than in the first measurement pump cell, the current can become the limiting current when oxygen is pumped out. That is, the second measurement pump cell is suitable for detecting the specific gas concentration if the concentration of the specific gas is higher than that in the first measurement pump cell. In contrast, the first measurement pump cell can cause a comparatively high limiting current to flow even if the concentration of the specific gas is low and thus is suitable for detecting the specific gas concentration that is lower than that in the second measurement pump cell. Thus, by selectively using the first measurement pump cell and the second measurement pump cell, the first sensor element can accurately detect the specific gas concentration in a broad range from a low concentration to a high concentration compared with, for example, a sensor element including only one of these measurement pump cells.

The first sensor element according to the present invention may include a reference electrode that is disposed within the element body and that contacts with a reference gas serving as a detection reference of the specific gas concentration in the measurement-object gas.

In the first sensor element according to the present invention, the first measurement-electrode diffusion-rate-controlling section may be a slit-like gap or a porous body, and the second measurement-electrode diffusion-rate-controlling section may be a slit-like gap or a porous body.

The first sensor element according to the present invention may further include, when n is an integer of greater than or equal to 3, first to n-th measurement pump cells including the first measurement pump cell and the second measurement pump cell, in which, when p is an integer from 3 to n, a p-th measurement pump cell may include a p-th measurement electrode and a p-th outer measurement electrode and may be configured to pump out oxygen produced in a p-th measurement chamber from the specific gas, the p-th measurement electrode being disposed in the p-th measurement chamber provided on a downstream side of the oxygen concentration adjustment chamber in the measurement-target-gas flow section, the p-th outer measurement electrode being provided outside the element body so as to contact with the measurement-object gas, and in which the measurement-object gas flow section may be configured such that the measurement-object gas passes through a (p−1)-th measurement chamber and a p-th measurement-electrode diffusion-rate-controlling section in this order and reaches the p-th measurement chamber. Thus, when a diffusion resistance of a route of the measurement-object gas from the outside of the sensor element to the p-th measurement electrode is a p-th diffusion resistance $R_p$, the p-th diffusion resistance $R_p$ is higher than a (p−1)-th diffusion resistance $R_{p-1}$, that is, $R_1 < R_2 < \ldots R_{n-1} < R_n$ is satisfied. Thus, by selectively using the first to n-th measurement pump cells, the first sensor element can accurately detect the specific gas concentration in a broader range (detection range of the specific gas concentration) compared with a sensor element including only the first and second measurement pump cells.

In this case, when k is an integer from 1 to n−1, a ratio $R_{k+1}/R_k$ between a k-th diffusion resistance $R_k$ and a (k+1)-th diffusion resistance $R_{k+1}$ may be greater than 1 and less than or equal to 100, the k-th diffusion resistance $R_k$ being a diffusion resistance of a route of the measurement-object gas from an outside to a k-th measurement electrode, the (k+1)-th diffusion resistance $R_{k+1}$ being a diffusion resistance of a route of the measurement-object gas from the outside to a (k+1)-th measurement electrode. That is, for each of the first to n-th measurement pump cells, the ratio of the diffusion resistance from the outside to a measurement electrode between adjacent measurement electrodes may be greater than 1 and less than or equal to 100. Note that, not only when n is greater than or equal to 3, but also when n is 2, this relationship may be satisfied. That is, if the sensor element includes only the first and second measurement pump cells as measurement pump cells, $R_2/R_1$ may be greater than 1 and less than or equal to 100.

A first gas sensor according to the present invention includes: the first sensor element according to any of the above-described embodiments; and a specific gas concentration detection device having a low concentration measurement mode and a high concentration measurement mode, the low concentration measurement mode being a mode on which the first measurement pump cell is controlled such that a pump current that flows in the first measurement pump cell becomes a limiting current, and, based on a value of the pump current, the specific gas concentration in the measurement-object gas is detected, the high concentration measurement mode being a mode on which the second measurement pump cell is controlled such that a pump current that flows in the second measurement pump cell becomes a limiting current, and, based on a value of the pump current, the specific gas concentration in the measurement-object gas is detected. This gas sensor detects the specific gas concentration in the measurement-object gas based on the value of the pump current that flows in the first measurement pump cell on the low concentration measurement mode and thus can accurately detect the specific gas concentration that is a low concentration. This gas sensor also detects the specific gas concentration in the measurement-object gas based on the value of the pump current that flows in the second measurement pump cell on the high concentration measurement mode and thus can accurately detect the specific gas concentration that is a high concentration.

In the first gas sensor according to the present invention, if the specific gas concentration detection device determines, based on the pump current that flows in the first measurement pump cell on the low concentration measurement mode, that the specific gas concentration in the measurement-object gas is included in a predetermined high concentration region, the specific gas concentration detection device may switch to the high concentration measurement mode, and, if the specific gas concentration detection device determines, based on the pump current that flows in the second measurement pump cell on the high concentration measurement mode, that the specific gas concentration in the measurement-object gas is included in a predetermined low concentration region, the specific gas concentration detection device may switch to the low concentration measurement mode. Thus, based on the pump currents, the low concentration measurement mode and the high concentration measurement mode can be switched appropriately.

In this case, the gas sensor may include a first measurement voltage detection device that detects a first measurement voltage between the reference electrode and the first measurement electrode and a second measurement voltage detection device that detects a second measurement voltage between the reference electrode and the second measurement electrode. In addition, the specific gas concentration detection device may control the first measurement pump cell based on the first measurement voltage on the low concentration measurement mode and may control the second measurement pump cell based on the second measurement voltage on the high concentration measurement mode. Alternatively, the specific gas concentration detection device may control the first measurement pump cell based on an average of the first measurement voltage and the second measurement voltage on the low concentration measurement mode and may control the second measurement pump cell based on the second measurement voltage on the high concentration measurement mode.

A second sensor element according to the present invention is
a sensor element for detecting an oxygen concentration as a concentration of a specific gas in a measurement-object gas, the sensor element including:
an element body including an oxygen-ion-conductive solid electrolyte layer and having a measurement-object gas flow section provided therein, the measurement-object gas flow section introducing the measurement-object gas and causing the measurement-object gas to flow;
a first measurement pump cell that includes a first measurement electrode and a first outer measurement electrode and that pumps out oxygen in the measurement-object gas, the first measurement electrode being disposed in a first measurement chamber in the measurement-object gas flow section, the first outer measurement electrode being provided outside the element body so as to contact with the measurement-object gas; and
a second measurement pump cell that includes a second measurement electrode and a second outer measurement electrode and that pumps out oxygen in the measurement-object gas, the second measurement electrode being disposed in a second measurement chamber in the measurement-object gas flow section, the second outer measurement electrode being provided outside the element body so as to contact with the measurement-object gas,
in which the measurement-object gas flow section is configured such that the measurement-object gas passes through the first measurement-electrode diffusion-rate-controlling section and reaches the first measurement chamber and that the measurement-object gas passes through the first measurement chamber and the second measurement-electrode diffusion-rate-controlling section in this order and reaches the second measurement chamber.

The second sensor element is a sensor element for detecting the oxygen concentration as the specific gas concentration. In substantially the same manner as that for the above-described first sensor element, the second sensor element is configured such that a second diffusion resistance $R_2$, which is a diffusion resistance of a route of the measurement-object gas from the outside of the sensor element to the second measurement electrode, is higher than a first diffusion resistance Ru which is a diffusion resistance of a route of the measurement-object gas from the outside of the sensor element to the first measurement electrode. Thus, by selectively using the first measurement pump cell and the second measurement pump cell, the second sensor element can also accurately detect the specific gas concentration in a broad range from a low concentration to a high concentration compared with, for example, a sensor element including only one of these measurement pump cells.

The second gas sensor according to the present invention includes: the above-described second sensor element; and a specific gas concentration detection device having a low concentration measurement mode and a high concentration measurement mode, the low concentration measurement mode being a mode on which the first measurement pump cell is controlled such that a pump current that flows in the first measurement pump cell becomes a limiting current, and, based on a value of the pump current, the specific gas concentration in the measurement-object gas is detected, the high concentration measurement mode being a mode on which the second measurement pump cell is controlled such that a pump current that flows in the second measurement pump cell becomes a limiting current, and, based on a value of the pump current, the specific gas concentration in the measurement-object gas is detected. In substantially the same manner as that of the above-described first gas sensor, the second gas sensor detects the specific gas concentration in the measurement-object gas based on the value of the pump current that flows in the first measurement pump cell on the low concentration measurement mode and thus can accurately detect the specific gas concentration that is a low concentration. The second gas sensor also detects the specific gas concentration in the measurement-object gas based on the value of the pump current that flows in the second measurement pump cell on the high concentration measurement mode and thus can accurately detect the specific gas concentration that is a high concentration.

The second sensor element according to the present invention may employ an embodiment that is substantially the same as various embodiments of the above-described first sensor element according to the present invention or may additionally employ a configuration that is substantially the same as the above-described first sensor element according to the present invention. The second gas sensor according to the present invention may employ an embodiment that is substantially the same as various embodiments of the above-described first gas sensor according to the present invention or may additionally employ a configuration that is substantially the same as the above-described first gas sensor according to the present invention.

BRIEF DESCRIPTION OF THE DRAWINGS

FIG. 4 illustrates an example of V-I characteristics of a first measurement pump cell 41a.

FIG. 5 illustrates an example of a correspondence relationship between a NOx concentration and a pump current Ip2a.

DETAILED DESCRIPTION OF THE INVENTION

Figure 1:
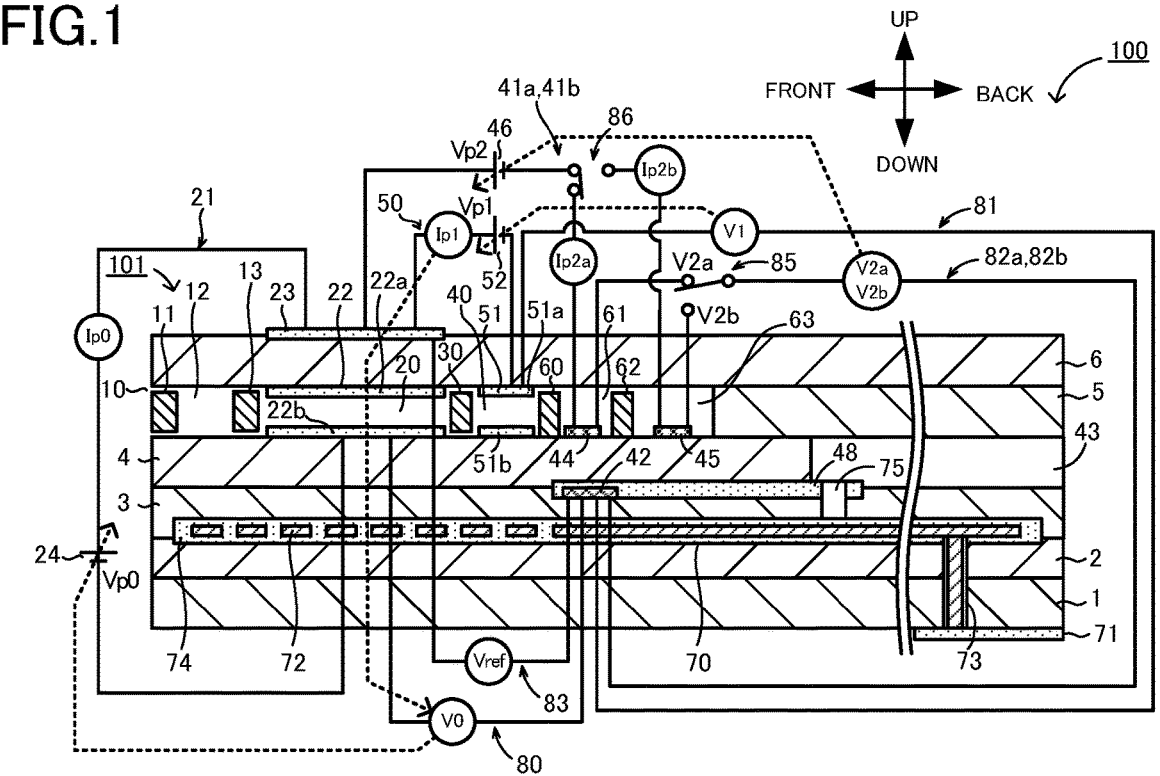
FIG. 1 is a schematic sectional view schematically illustrating an example of the configuration of a gas sensor 100.
Figure 2:
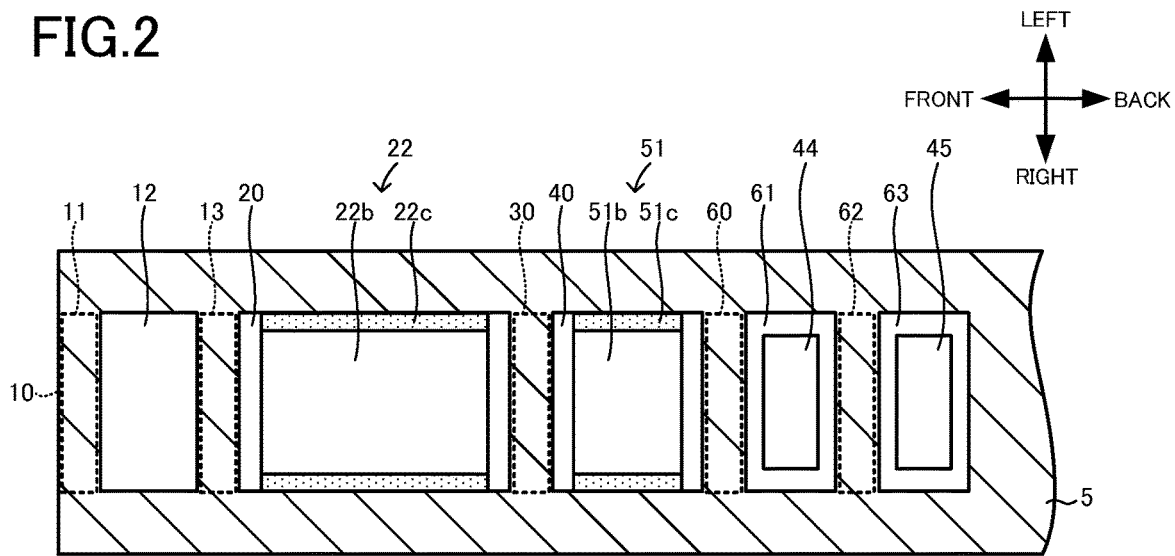
FIG. 2 is a schematic sectional view of a measurement-object gas flow section.
Figure 3:
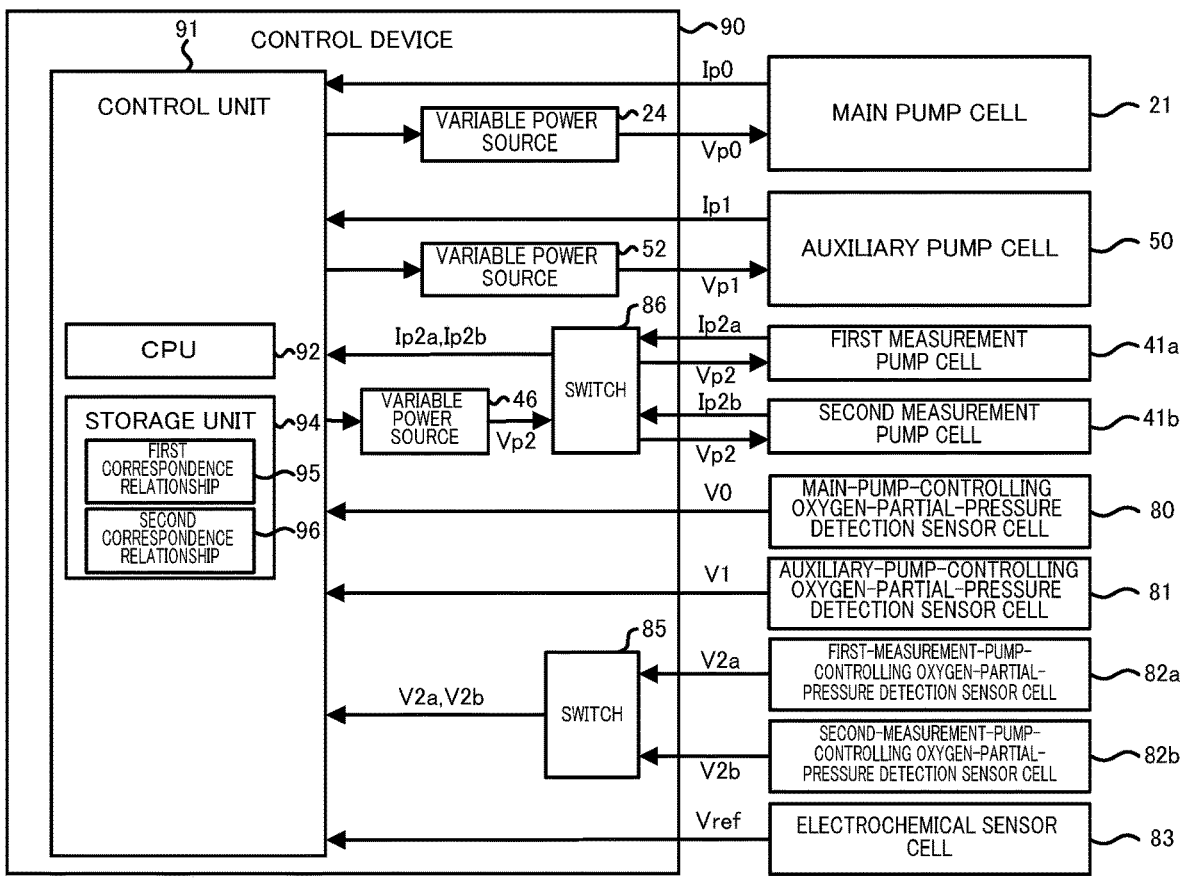
FIG. 3 is a block diagram illustrating an electrical connection relationship between a control device 90 and each cell.

Now, an embodiment of the present invention will be described with reference to the drawings. FIG. 1 is a schematic sectional view schematically illustrating an example of the configuration of a gas sensor 100 according to an embodiment of the present invention. FIG. 2 is a schematic sectional view of a measurement-object gas flow section. FIG. 3 is a block diagram illustrating an electrical connection relationship between a control device 90 and each cell. FIG. 2 illustrates a partial section along the front-to-back direction and the horizontal direction of a spacer layer 5 in a sensor element 101. The gas sensor 100 is attached to, for example, a pipe such as an exhaust gas pipe of an internal combustion engine. The gas sensor 100 detects the concentration of a specific gas such as NOx or ammonia in a measurement-object gas that is exhaust gas of the internal combustion engine. In this embodiment, the gas sensor 100 measures an NOx concentration as a specific gas concentration. The gas sensor 100 includes the sensor element 101 having an elongated cuboid form, cells 21, 41a, 41b, 50, 80, 81, 82a, 82b, and 83 included in the sensor element 101, and the control device 90 that has variable power sources 24, 46, and 52 and switches 85 and 86 and that controls the entirety of the gas sensor 100.

The sensor element 101 is an element having a layered body of six layers each of which is formed of an oxygen-ion-conductive solid electrolyte layer of zirconia ($ZrO_2$) or the like. The six layers are a first substrate layer 1, a second substrate layer 2, a third substrate layer 3, a first solid electrolyte layer 4, the spacer layer 5, and a second solid electrolyte layer 6, and are layered in this order from the bottom in FIG. 1. In addition, the solid electrolyte forming these six layers is dense and gas-tight. For example, ceramic green sheets corresponding to the respective layers are subjected to predetermined processing, circuit pattern printing, and the like, and these sheets are layered and then further fired to manufacture the sensor element 101 as a single form.

On the tip side (left end side in FIG. 1) of the sensor element 101 between the lower surface of the second solid electrolyte layer 6 and the upper surface of the first solid electrolyte layer 4, a gas inlet 10, a first diffusion-rate-controlling section 11, a buffer space 12, a second diffusion-rate-controlling section 13, a first internal cavity 20, a third diffusion-rate-controlling section 30, a second internal cavity 40, a fourth diffusion-rate-controlling section 60, a third internal cavity 61, a fifth diffusion-rate-controlling section 62, and a fourth internal cavity 63 are formed adjacent to one another to communicate in this order.

The gas inlet 10, the buffer space 12, the first internal cavity 20, the second internal cavity 40, the third internal cavity 61, and the fourth internal cavity 63 form a space inside the sensor element 101. The space is formed by hollowing the spacer layer 5, with the top thereof defined by the lower surface of the second solid electrolyte layer 6, the bottom thereof defined by the upper surface of the first solid electrolyte layer 4, and a side thereof defined by a side surface of the spacer layer 5.

The first diffusion-rate-controlling section 11, the second diffusion-rate-controlling section 13, and the third diffusion-rate-controlling section 30 are each provided as two horizontally long slits (with openings having a longitudinal direction in the direction perpendicular to the drawing in FIG. 1) (see also FIG. 2). In addition, the fourth diffusion-rate-controlling section 60 and the fifth diffusion-rate-controlling section 62 are each provided as a single horizontally long slit (with an opening having a longitudinal direction in the direction perpendicular to the drawing in FIG. 1) formed as a gap from the lower surface of the second solid electrolyte layer 6 (see also FIG. 2). Note that the part from the gas inlet 10 to the fourth internal cavity 63 is also referred to as measurement-object gas flow section.

Beyond the measurement-object gas flow section from the tip side, a reference-gas introduction space 43 is provided at a position between the upper surface of the third substrate layer 3 and the lower surface of the spacer layer 5, with a side thereof being defined by a side surface of the first solid electrolyte layer 4. As a reference gas for measuring the NOx concentration, for example, atmospheric air is introduced into the reference-gas introduction space 43.

An atmospheric-air introduction layer 48 is formed of porous ceramics, and the reference gas is introduced into the atmospheric-air introduction layer 48 through the reference-gas introduction space 43. In addition, the atmospheric-air introduction layer 48 is formed to cover a reference electrode 42.

The reference electrode 42 is an electrode formed to be sandwiched between the upper surface of the third substrate layer 3 and the first solid electrolyte layer 4. As described above, the reference electrode 42 is surrounded by the atmospheric-air introduction layer 48 connected to the reference-gas introduction space 43. In addition, as will be described later, the reference electrode 42 can be used to measure the oxygen concentrations (oxygen partial pressures) within the first internal cavity 20, the second internal cavity 40, the third internal cavity 61, and the fourth internal cavity 63. The reference electrode 42 is formed as a porous cermet electrode (e.g., cermet electrode of Pt and $ZrO_2$).

In the measurement-object gas flow section, the gas inlet 10 is a part open to an external space, and the measurement-object gas is taken into the sensor element 101 from the external space through the gas inlet 10. The first diffusion-rate-controlling section 11 is a part that applies a predetermined diffusion resistance to the measurement-object gas taken through the gas inlet 10. The buffer space 12 is a space provided for guiding the measurement-object gas introduced from the first diffusion-rate-controlling section 11 to the second diffusion-rate-controlling section 13. The second diffusion-rate-controlling section 13 is a part that applies a predetermined diffusion resistance to the measurement-object gas introduced from the buffer space 12 into the first internal cavity 20. When the measurement-object gas is introduced from the outside of the sensor element 101 into the first internal cavity 20, the measurement-object gas, which is rapidly taken into the sensor element 101 through the gas inlet 10 due to changes in the pressure of the measurement-object gas in the external space (pulsations in exhaust pressure when the measurement-object gas is exhaust gas of an automobile), is not directly introduced into the first internal cavity 20, but is introduced into the first internal cavity 20 after the changes in the pressure of the measurement-object gas are compensated for through the first diffusion-rate-controlling section 11, the buffer space 12, and the second diffusion-rate-controlling section 13. Thus, the changes in the pressure of the measurement-object gas to be introduced into the first internal cavity 20 are almost negligible. The first internal cavity 20 is provided as a space for adjusting the oxygen partial pressure in the measurement-object gas that is introduced through the second diffusion-rate-controlling section 13. The oxygen partial pressure is adjusted by the operation of the main pump cell 21.

The main pump cell 21 is an electrochemical pump cell including an inner pump electrode 22, an outer pump electrode 23, and the second solid electrolyte layer 6 sandwiched between these electrodes. The inner pump electrode 22 has a ceiling electrode portion 22a provided on substantially the entire surface of the lower surface of the second solid electrolyte layer 6 facing the first internal cavity 20. The outer pump electrode 23 is provided to be exposed to the external space in a region corresponding to the ceiling electrode portion 22a on the top surface of the second solid electrolyte layer 6.

The inner pump electrode 22 is formed across the upper and lower solid electrolyte layers (the second solid electrolyte layer 6 and the first solid electrolyte layer 4) defining the first internal cavity 20 and the spacer layer 5 forming the sidewalls. Specifically, the ceiling electrode portion 22a is formed on the lower surface of the second solid electrolyte layer 6 that forms the ceiling surface of the first internal cavity 20, and a bottom electrode portion 22b is formed on the upper surface of the first solid electrolyte layer 4 that forms the bottom surface of the first internal cavity 20. Furthermore, to connect the ceiling electrode portion 22a and the bottom electrode portion 22b to each other, side electrode portions 22c (see FIG. 2) are formed on sidewall surfaces (inner surfaces) of the spacer layer 5 forming both sidewall portions of the first internal cavity 20. The inner pump electrode 22 is disposed to have a tunnel structure in the part where the side electrode portions 22c are disposed.

The inner pump electrode 22 and the outer pump electrode 23 are each formed as a porous cermet electrode (e.g., cermet electrode of Pt and $ZrO_2$ containing Au at 1%). Note that the inner pump electrode 22 to contact with the measurement-object gas is formed of a material whose reduction ability for NOx components in the measurement-object gas is decreased.

By applying a desired voltage Vp0 between the inner pump electrode 22 and the outer pump electrode 23 to cause a pump current Ip0 to flow between the inner pump electrode 22 and the outer pump electrode 23 in the positive direction or in the negative direction, so that the main pump cell 21 can pump out oxygen from the first internal cavity 20 to the external space or can pump in oxygen from the external space to the first internal cavity 20.

In addition, in order to detect the oxygen concentration (oxygen partial pressure) in the atmosphere in the first internal cavity 20, an electrochemical sensor cell, that is, a main-pump-controlling oxygen-partial-pressure detection sensor cell 80, is formed by the inner pump electrode 22, the second solid electrolyte layer 6, the spacer layer 5, the first solid electrolyte layer 4, the third substrate layer 3, and the reference electrode 42.

The oxygen concentration (oxygen partial pressure) within the first internal cavity 20 is determined by measuring an electromotive force (voltage V0) in the main-pump-controlling oxygen-partial-pressure detection sensor cell 80. In addition, the pump current Ip0 is controlled by feed-back control of the voltage Vp0 of the variable power source 24 such that the voltage V0 becomes a target value. Thus, the oxygen concentration within the first internal cavity 20 can be maintained at a predetermined constant value.

The third diffusion-rate-controlling section 30 is a part that applies a predetermined diffusion resistance to the measurement-object gas in which the oxygen concentration (oxygen partial pressure) is controlled by the operation of the main pump cell 21 within the first internal cavity 20. The third diffusion-rate-controlling section 30 guides the measurement-object gas to the second internal cavity 40.

The second internal cavity 40 is provided as a space for further adjusting, by using an auxiliary pump cell 50, the oxygen partial pressure of the measurement-object gas that has been subjected to oxygen concentration (oxygen partial pressure) adjustment in advance within the first internal cavity 20 and is then introduced through the third diffusion-rate-controlling section 30. Thus, the oxygen concentration within the second internal cavity 40 can be maintained constant with high accuracy, and this enables the gas sensor 100 to accurately measure the NOx concentration.

The auxiliary pump cell 50 is an auxiliary electrochemical pump cell including an auxiliary pump electrode 51, the outer pump electrode 23 (not limited to the outer pump electrode 23, and an appropriate electrode outside the sensor element 101 may suffice), and the second solid electrolyte layer 6. The auxiliary pump electrode 50 has a ceiling electrode portion 51a provided on substantially the entire lower surface of the second solid electrolyte layer 6 facing the second internal cavity 40.

The auxiliary pump electrode 51 is disposed within the second internal cavity 40 to have a tunnel structure that is substantially the same as that of the above inner pump electrode 22 provided within the first internal cavity 20. That is, the ceiling electrode portion 51a is formed on the second solid electrolyte layer 6 that forms the ceiling surface of the second internal cavity 40, and a bottom electrode portion 51b is formed on the first solid electrolyte layer 4 that forms the bottom surface of the second internal cavity 40. Furthermore, side electrode portions 51c (see FIG. 2) that connects the ceiling electrode portion 51a and the bottom electrode portion 51b to each other are formed on both sidewall surfaces of the spacer layer 5 forming sidewalls of the second internal cavity 40. The auxiliary pump electrode 51 has a tunnel structure. Note that, as in the inner pump electrode 22, the auxiliary pump electrode 51 is formed of a material whose reduction ability for NOx components in the measurement-object gas is decreased.

By applying a desired voltage Vp1 between the auxiliary pump electrode 51 and the outer pump electrode 23, the auxiliary pump cell 50 can pump out oxygen from the second internal cavity 40 to the external space or can pump in oxygen from the external space to the second internal cavity 40.

In addition, in order to control the oxygen partial pressure in the atmosphere in the second internal cavity 40, an electrochemical sensor cell, that is, an auxiliary-pump-controlling oxygen-partial-pressure detection sensor cell 81, is formed by the auxiliary pump electrode 51, the reference electrode 42, the second solid electrolyte layer 6, the spacer layer 5, the first solid electrolyte layer 4, and the third substrate layer 3.

Note that the auxiliary pump cell 50 performs pumping at the variable power source 52 whose voltage is controlled based on an electromotive force (voltage V1) detected by the auxiliary-pump-controlling oxygen-partial-pressure detection sensor cell 81. Thus, the oxygen partial pressure in the atmosphere within the second internal cavity 40 is controlled to a low partial pressure that does not substantially affect NOx measurement.

In addition, along with this, a pump current Ip1 thereof is used to control the electromotive force of the main-pump-controlling oxygen-partial-pressure detection sensor cell 80. Specifically, the pump current Ip1 is input to the main-pump-controlling oxygen-partial-pressure detection sensor cell 80 as a control signal, and the above target value of the voltage V0 thereof is controlled, so that the gradient of the oxygen partial pressure in the measurement-object gas introduced from the third diffusion-rate-controlling section 30 into the second internal cavity 40 is controlled to be always constant. In a case of usage as an NOx sensor, the oxygen partial pressure within the second internal cavity 40 is maintained at a constant value of about 0.001 ppm by the operation of the main pump cell 21 and the auxiliary pump cell 50. The first internal cavity 20 and the second internal cavity 40 are each an example of an oxygen concentration adjustment chamber, and the main pump cell 21 and the auxiliary pump cell 50 are each an example of an adjustment pump cell.

The fourth diffusion-rate-controlling section 60 is a part that applies a predetermined diffusion resistance to the measurement-object gas in which the oxygen concentration (oxygen partial pressure) is controlled by the operation of the auxiliary pump cell 50 within the second internal cavity 40. The fourth diffusion-rate-controlling section 60 guides the measurement-object gas to the third internal cavity 61. The fourth diffusion-rate-controlling section 60 has a role of limiting the amount of NOx flowing into the third internal cavity 61.

The third internal cavity 61 is provided as a space for performing processing related to measurement of the nitrogen oxide (NOx) concentration in the measurement-object gas on the measurement-object gas that has been subjected to oxygen concentration (oxygen partial pressure) adjustment in advance within the second internal cavity 40 and is then introduced through the fourth diffusion-rate-controlling section 60. The fourth internal cavity 63 is provided as a space for performing processing related to measurement of the nitrogen oxide (NOx) concentration in the measurement-object gas on the measurement-object gas that has been subjected to oxygen concentration (oxygen partial pressure) adjustment in advance within the second internal cavity 40 and is then introduced through the fourth diffusion-rate-controlling section 60 and the fifth diffusion-rate-controlling section 62. The measurement of the NOx concentration is mainly performed by any of the operation of a first measurement pump cell 41a in the third internal cavity 61 and the operation of a second measurement pump cell 41b in the fourth internal cavity 63. As will be described later in detail, the first measurement pump cell 41a is suitable for detecting the NOx concentration that is a comparatively low concentration, and the second measurement pump cell 41b is suitable for detecting the NOx concentration that is a comparatively high concentration. The fourth diffusion-rate-controlling section 60 is an example of a first measurement-electrode diffusion-rate-controlling section, and the fifth diffusion-rate-controlling section 62 is an example of a second measurement-electrode diffusion-rate-controlling section. The third internal cavity 61 is an example of a first measurement chamber, and the fourth internal cavity 63 is an example of a second measurement chamber.

The first measurement pump cell 41a measures the NOx concentration in the measurement-object gas within the third internal cavity 61. The first measurement pump cell 41a is an electrochemical pump cell including a first measurement electrode 44 provided on the upper surface of the first solid electrolyte layer 4 facing the third internal cavity 61, the outer pump electrode 23, the second solid electrolyte layer 6, the spacer layer 5, and the first solid electrolyte layer 4. The second measurement pump cell 41b measures the NOx concentration in the measurement-object gas within the fourth internal cavity 63. The second measurement pump cell 41b is an electrochemical pump cell including a second measurement electrode 45 provided on the upper surface of the first solid electrolyte layer 4 facing the fourth internal cavity 63, the outer pump electrode 23, the second solid electrolyte layer 6, the spacer layer 5, and the first solid electrolyte layer 4. The first measurement electrode 44 and the second measurement electrode 45 are porous cermet electrodes formed of a material whose reduction ability for NOx components in the measurement-object gas is increased to be higher than that of the inner pump electrode 22. The first measurement electrode 44 also serves as an NOx reducing catalyst for reducing NOx that is present in the atmosphere within the third internal cavity 61. The second measurement electrode 45 also serves as an NOx reducing catalyst for reducing NOx that is present in the atmosphere within the fourth internal cavity 63.

The first measurement pump cell 41a can pump out oxygen produced by decomposition of nitrogen oxide in the atmosphere around the first measurement electrode 44 and can detect the amount of produced oxygen as a pump current Ip2a. The second measurement pump cell 41b can pump out oxygen produced by decomposition of nitrogen oxide in the atmosphere around the second measurement electrode 45 and can detect the amount of produced oxygen as a pump current Ip2b.

In addition, in order to detect the oxygen partial pressure around the first measurement electrode 44, an electrochemical sensor cell, that is, a first-measurement-pump-controlling oxygen-partial-pressure detection sensor cell 82a is formed by the first solid electrolyte layer 4, the third substrate layer 3, the first measurement electrode 44, and the reference electrode 42. Similarly, in order to detect the oxygen partial pressure around the second measurement electrode 45, an electrochemical sensor cell, that is, a second-measurement-pump-controlling oxygen-partial-pressure detection sensor cell 82b is formed by the first solid electrolyte layer 4, the third substrate layer 3, the second measurement electrode 45, and the reference electrode 42. The variable power source 46 is controlled based on one of an electromotive force (voltage V2a) detected by the first-measurement-pump-controlling oxygen-partial-pressure detection sensor cell 82a and an electromotive force (voltage V2b) detected by the second-measurement-pump-controlling oxygen-partial-pressure detection sensor cell 82b.

Now, a case of using the first measurement pump cell 41a will be described. The measurement-object gas that has been guided into the second internal cavity 40, in which the oxygen partial pressure is controlled, passes through the fourth diffusion-rate-controlling section 60 and reaches the first measurement electrode 44 within the third internal cavity 61. In the measurement-object gas around the first measurement electrode 44, nitrogen oxide is reduced to produce oxygen ($2NO \rightarrow N_2 + O_2$). The produced oxygen is subjected to pumping by the first measurement pump cell 41a. In this process, a voltage Vp2 of the variable power source 46 is controlled so that the voltage V2a detected by the first-measurement-pump-controlling oxygen-partial-pressure detection sensor cell 82a becomes constant (target value). Since the amount of oxygen produced around the first measurement electrode 44 is proportional to the concentration of nitrogen oxide in the measurement-object gas, the nitrogen oxide concentration in the measurement-object gas is calculated using the pump current Ip2a in the first measurement pump cell 41a.

A case of using the second measurement pump cell 41b is substantially the same as above. That is, first, the measurement-object gas that has been guided into the second internal cavity 40, in which the oxygen partial pressure is controlled, passes through the fourth diffusion-rate-controlling section 60 and the fifth diffusion-rate-controlling section 62 and reaches the second measurement electrode 45 within the fourth internal cavity 63. In the measurement-object gas around the second measurement electrode 45, nitrogen oxide is reduced to produce oxygen ($2NO \rightarrow N_2 + O_2$). The produced oxygen is subjected to pumping by the second measurement pump cell 41b. In this process, the voltage Vp2 of the variable power source 46 is controlled so that the voltage V2b detected by the second-measurement-pump-controlling oxygen-partial-pressure detection sensor cell 82b becomes constant (target value). Since the amount of oxygen produced around the second measurement electrode 45 is proportional to the concentration of nitrogen oxide in the measurement-object gas, the nitrogen oxide concentration in the measurement-object gas is calculated using the pump current Ip2b in the second measurement pump cell 41b.

In addition, an electrochemical sensor cell 83 is formed by the second solid electrolyte layer 6, the spacer layer 5, the first solid electrolyte layer 4, the third substrate layer 3, the outer pump electrode 23, and the reference electrode 42. Based on an electromotive force (voltage Vref) obtained by the sensor cell 83, the oxygen partial pressure in the measurement-object gas outside the sensor can be detected.

In the gas sensor 100 having such a configuration, the main pump cell 21 and the auxiliary pump cell 50 are activated to provide the first measurement pump cell 41a and the second measurement pump cell 41b with the measurement-object gas in which the oxygen partial pressure is always maintained at a constant low value (a value that does not substantially affect NOx measurement). Accordingly, the NOx concentration in the measurement-object gas can be determined based on the pump current Ip2a or the pump current Ip2b caused to flow by the first measurement pump cell 41a or the second measurement pump cell 41b pumping out oxygen produced by reducing NOx approximately in proportion to the NOx concentration in measurement-object gas.

The sensor element 101 further includes a heater unit 70 that has a role of adjusting temperatures to heat the sensor element 101 and keep the sensor element 101 warm to enhance the oxygen ion conductivity of the solid electrolyte. The heater unit 70 includes a heater connector electrode 71, a heater 72, a through hole 73, a heater insulating layer 74, and a pressure release hole 75.

The heater connector electrode 71 is an electrode formed in contact with the lower surface of the first substrate layer 1. Connecting the heater connector electrode 71 to an external power source allows power to be fed to the heater unit 70 from the outside.

The heater 72 is an electric resistor formed to be vertically held between the second substrate layer 2 and the third substrate layer 3. The heater 72 is connected to the heater connector electrode 71 via the through hole 73. The heater 72 generates heat in response to power fed thereto from the outside through the heater connector electrode 71 to heat the solid electrolyte forming the sensor element 101 and keep the solid electrolyte warm.

The heater 72 is embedded across an entire area from the first internal cavity 20 to the third internal cavity 61 and can adjust the temperature of the entire sensor element 101 to a temperature at which the solid electrolyte is active.

The heater insulating layer 74 is an insulating layer formed of an insulator such as alumina on the upper and lower surfaces of the heater 72. The heater insulating layer 74 is formed to provide electrical insulation between the second substrate layer 2 and the heater 72 and electrical insulation between the third substrate layer 3 and the heater 72.

The pressure release hole 75 is a part provided so as to extend through the third substrate layer 3 and the atmospheric-air introduction layer 48 and communicate with the reference-gas introduction space 43. The pressure release hole 75 is formed to mitigate an increase in internal pressure caused by a temperature rise in the heater insulating layer 74.

The control device 90 includes the above-described variable power sources 24, 46, and 52, the switches 85 and 86 for switching whether any of the first measurement pump cell 41a and the second measurement pump cell 41b is controlled, and a control unit 91. The control unit 91 is a microprocessor including a CPU 92, a RAM that is not illustrated, a storage unit 94, and so on. The storage unit 94 is, for example, a nonvolatile memory such as ROM and is a device storing various kinds of data. The control unit 91 receives the voltage V0 detected by the main-pump-controlling oxygen-partial-pressure detection sensor cell 80, the voltage V1 detected by the auxiliary-pump-controlling oxygen-partial-pressure detection sensor cell 81, the voltage Vref detected by the sensor cell 83, the pump current Ip0 detected by the main pump cell 21, and the pump current Ip1 detected by the auxiliary pump cell 50. The control unit 91 outputs a control signal to the variable power sources 24 and 52 to control the voltages Vp0 and Vp1 output from the variable power sources 24 and 52, thereby controlling the main pump cell 21 and the auxiliary pump cell 50. By switching a circuit electrical connection by using the switch 85, the control unit 91 selectively receives one of the voltage V2a detected by the first-measurement-pump-controlling oxygen-partial-pressure detection sensor cell 82a and the voltage V2b detected by the second-measurement-pump-controlling oxygen-partial-pressure detection sensor cell 82b. In addition, by switching a circuit electrical connection by using the switch 86, the control unit 91 selectively switches whether the control target is any of the first measurement pump cell 41a and the second measurement pump cell 41b. Specifically, by switching the switch 86, the control unit 91 switches whether to apply the voltage Vp2 of the variable power source 46 to any of the first measurement pump cell 41a and the second measurement pump cell 41b and also switches to receive any of the pump current Ip2a flowing in the first measurement pump cell 41a and the pump current Ip2b flowing in the second measurement pump cell 41b. The storage unit 94 also stores target values V0*, V1*, and V2*, which will be described later. By referring to these target values V0*, V1*, and V2*, the CPU 92 of the control unit 91 controls the cells 21, 41a, 41b, and 50. The CPU 92 also controls the heater 72.

The control unit 91 performs feedback control of the voltage Vp0 of the variable power source 24 so that the voltage V0 becomes a target value (referred to as target value V0*) (i.e., the oxygen concentration in the first internal cavity 20 becomes a target concentration).

The control unit 91 also performs feedback control of the voltage Vp1 of the variable power source 52 so that the voltage V1 becomes a constant value (referred to as target value V1*) (i.e., the oxygen concentration in the second internal cavity 40 becomes a predetermined low oxygen concentration that does not substantially affect NOx measurement). Additionally, the control unit 91 sets (performs feedback control of) the target value V0* of the voltage V0, based on the pump current Ip1 so that the pump current Ip1 caused to flow by the voltage Vp1 becomes a constant value (referred to as a target value Ip1*). Accordingly, the gradient of the oxygen partial pressure in the measurement-object gas to be introduced into the second internal cavity 40 from the third diffusion-rate-controlling section 30 remains always constant. In addition, the oxygen partial pressure in the atmosphere in the second internal cavity 40 is controlled to a low partial pressure that does not substantially affect NOx measurement. The target value V0* is set to a value such that the oxygen concentration in the first internal cavity 20 becomes a low oxygen concentration of higher than 0%.

The control unit 91 has a low concentration measurement mode and a high concentration measurement mode. The low concentration measurement mode is a measurement mode suitable for the measurement-object gas with the NOx concentration that is a comparatively low concentration, and the high concentration measurement mode is a measurement mode suitable for the measurement-object gas with the NOx concentration that is a comparatively high concentration.

On the low concentration measurement mode, the control unit 91 controls the first measurement pump cell 41a such that the pump current Ip2a becomes the limiting current and detects, based on the value of the pump current Ip2a flowing at this time, the specific gas concentration in the measurement-object gas. Specifically, first, the control unit 91 performs feedback control of the voltage Vp2 of the variable power source 46 such that the voltage V2a becomes a constant value (referred to as target value V2*) (i.e., the oxygen concentration within the third internal cavity 61 becomes a predetermined low concentration). The target value V2* is determined in advance as a value by which the pump current Ip2a that is caused to flow by the voltage Vp2 subjected to feedback control becomes the limiting current. By the pump current Ip2a being caused to flow, oxygen is pumped out from the third internal cavity 61 so that oxygen produced by reduction of NOx in the measurement-object gas within the third internal cavity 61 becomes substantially zero. Then, the control unit 91 acquires the pump current Ip2a as a detection value in accordance with oxygen that is produced in the third internal cavity 61 that is derived from a specific gas (here, NOx), and, based on the pump current Ip2a, calculates the NOx concentration in the measurement-object gas. In this embodiment, the storage unit 94 stores in advance a first correspondence relationship 95 representing a correspondence relationship between the pump current Ip2a and the NOx concentration. Based on the acquired pump current Ip2a and the first correspondence relationship 95, the control unit 91 calculates the NOx concentration. The first correspondence relationship 95 is data such as a relation formula (e.g., linear function formula) or a map.

On the high concentration measurement mode, the control unit 91 controls the second measurement pump cell 41b such that the pump current Ip2b becomes the limiting current and detects, based on the value of the pump current Ip2b flowing at this time, the specific gas concentration in the measurement-object gas. On the high concentration measurement mode, the control unit 91 performs substantially the same control as that on the low concentration measurement mode except that the second measurement pump cell 41b is controlled based on the voltage V2b. Specifically, first, the control unit 91 performs feedback control of the voltage Vp2 of the variable power source 46 such that the voltage V2b becomes a constant value (target value V2*) (i.e., the oxygen concentration within the fourth internal cavity 63 becomes a predetermined low concentration). The target value V2* is determined in advance as a value by which the pump current Ip2b that is caused to flow by the voltage Vp2 subjected to feedback control becomes the limiting current. The target value V2* on the high concentration measurement mode is equal to the target value V2* on the low concentration measurement mode. However, the target value V2* may be different values between the high concentration measurement mode and the low concentration measurement mode. By the pump current Ip2b being caused to flow, oxygen is pumped out from the fourth internal cavity 63 so that oxygen produced by reduction of NOx in the measurement-object gas within the fourth internal cavity 63 becomes substantially zero. Then, the control unit 91 acquires the pump current Ip2b as a detection value in accordance with oxygen that is produced in the fourth internal cavity 63 and that is derived from a specific gas (here, NOx), and, based on the pump current Ip2b, calculates the NOx concentration in the measurement-object gas. In this embodiment, the storage unit 94 stores in advance a second correspondence relationship 96 representing a correspondence relationship between the pump current Ip2b and the NOx concentration. Based on the acquired pump current Ip2b and the second correspondence relationship 96, the control unit 91 calculates the NOx concentration. The second correspondence relationship 96 is data such as a relation formula (e.g., linear function formula) or a map.

In the above manner, oxygen derived from the specific gas in the measurement-object gas that has been introduced into the sensor element 101 is pumped out, and, based on the limiting current (here, the pump currents Ip2a and Ip2b) that flows when the oxygen is pumped out, the specific gas concentration is detected. This method is referred to as limiting-current method.

Figure 4:
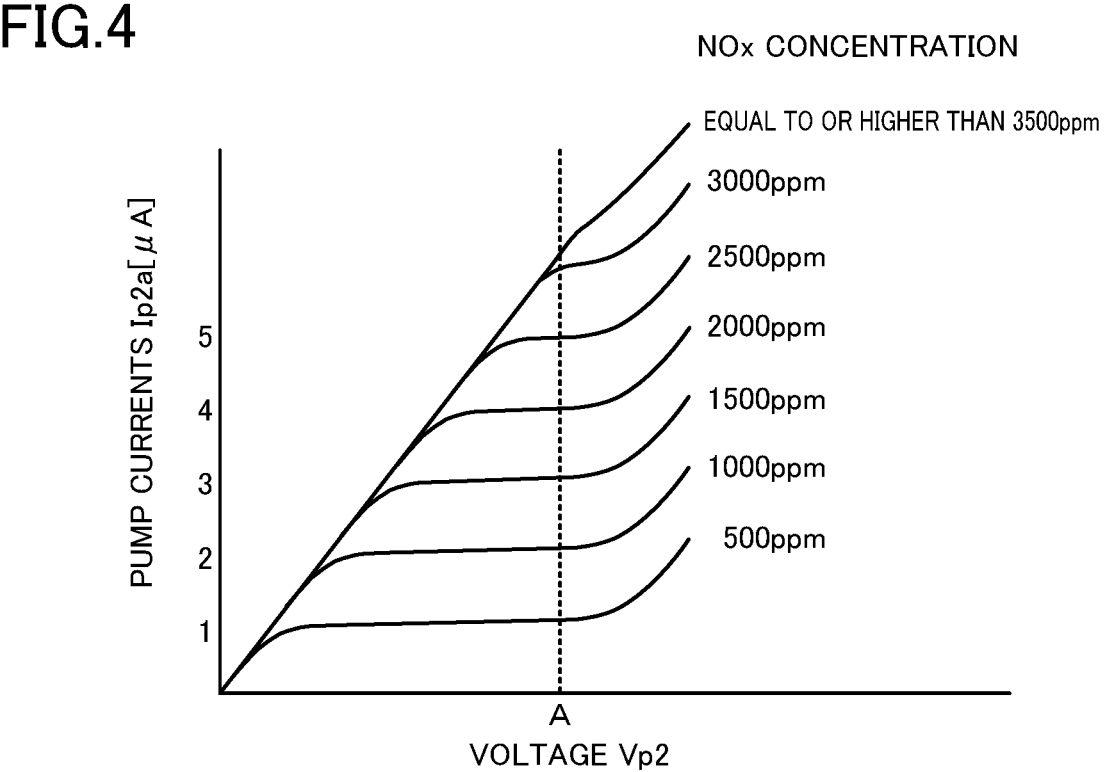
Figure 5:
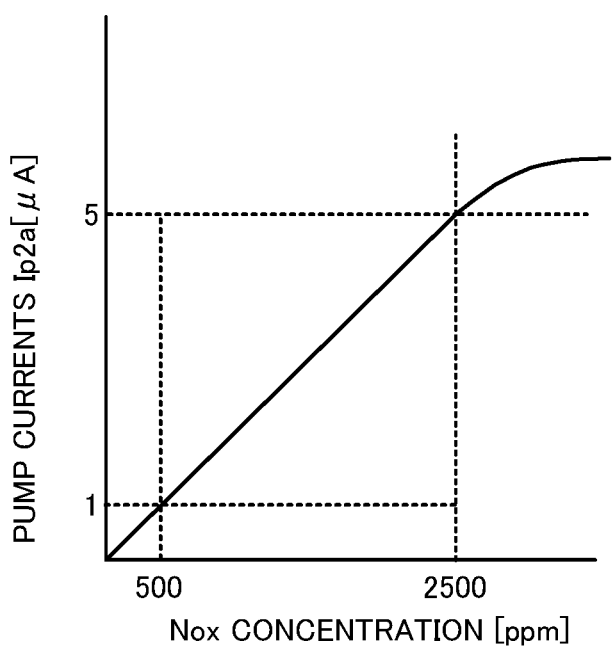
Figure 6:
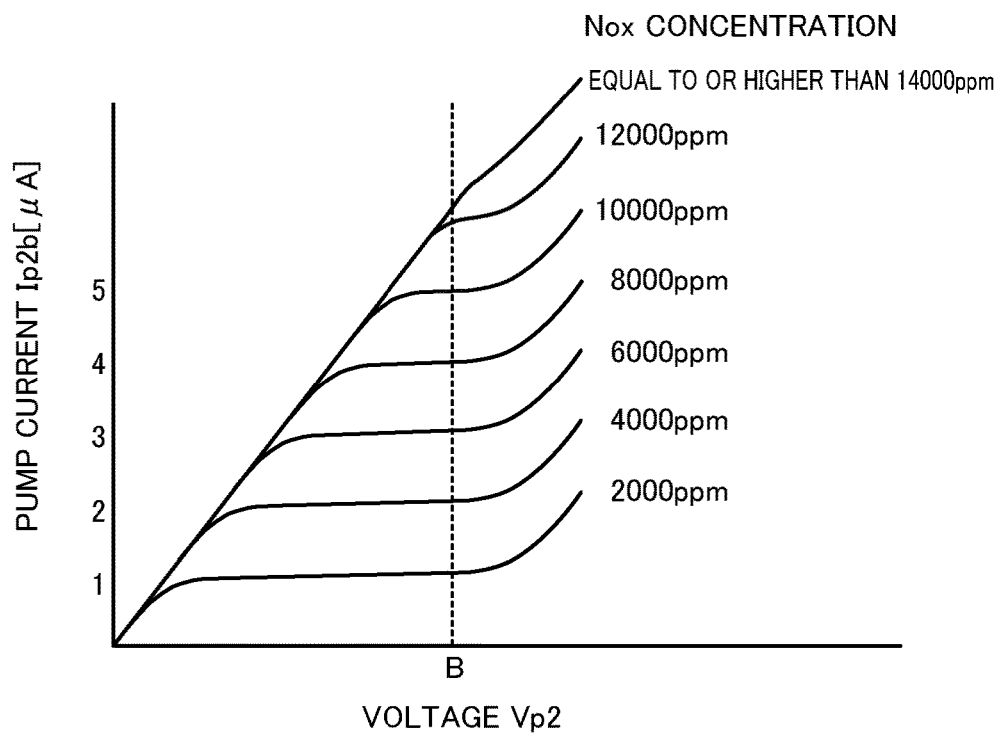
FIG. 6 illustrates an example of V-I characteristics of a second measurement pump cell 41b.
Figure 7:
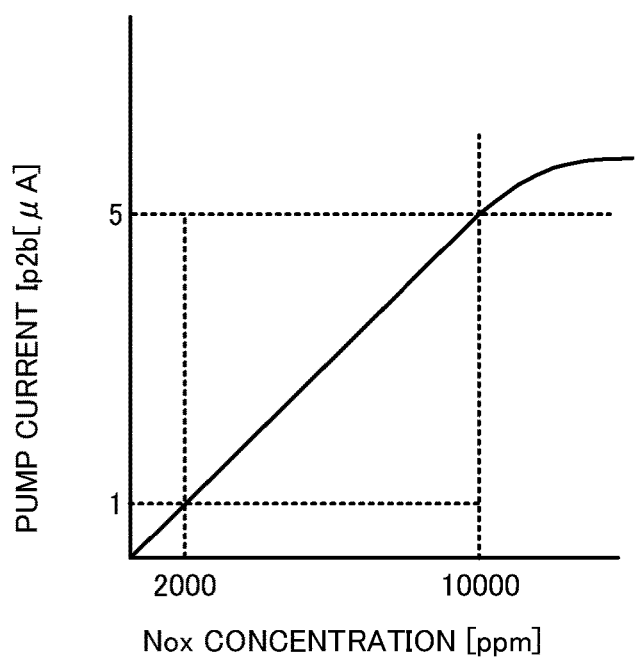
FIG. 7 illustrates an example of a correspondence relationship between a NOx concentration and a pump current Ip2b.

Now, operation characteristics of the first measurement pump cell 41a and the second measurement pump cell 41b will be described. FIG. 4 illustrates an example of a relationship between the voltage Vp2 and the pump current Ip2a (V-I characteristics) in the first measurement pump cell 41a, and FIG. 5 illustrates an example of the correspondence relationship between the NOx concentration and the pump current Ip2a. FIG. 6 illustrates an example of a relationship between the voltage Vp2 and the pump current Ip2b (V-I characteristics) in the second measurement pump cell 41b, and FIG. 7 illustrates an example of the correspondence relationship between the NOx concentration and the pump current Ip2b. FIG. 5 illustrates a relationship between the NOx concentration and the pump current Ip2a in a case in which the voltage Vp2 is a value A (see FIG. 4), and FIG. 7 illustrates a relationship between the NOx concentration and the pump current Ip2b in a case in which the voltage Vp2 is a value B (see FIG. 6).

As illustrated in FIG. 4, in the first measurement pump cell 41a, in a region where the voltage Vp2 is low, the pump current Ip2a increases in accordance with an increase in the voltage Vp2. In a region where the voltage Vp2 is high to some extent, by the influence of the diffusion resistance of the measurement-object gas flow section, even if the voltage Vp2 changes, the increase in the pump current Ip2a is gentle, and the pump current Ip2a is substantially a constant value. That is, the pump current Ip2a becomes the limiting current. This region is called plateau region. In a region where the voltage Vp2 is higher than that in the plateau region, for example, if the measurement-object gas contains moisture, the moisture is decomposed to produce oxygen. Thus, the pump current Ip2a increases again in accordance with the increase in the voltage Vp2. In addition, the higher the NOx concentration in the measurement-object gas, the larger the value of the limiting current is. For example, the value of the limiting current (the pump current Ip2a) in FIG. 4 is about 1 μA if the NOx concentration is 500 ppm and is about 5 μA if the NOx concentration is 2500 ppm. Thus, for example, if, based on the target value V2*, the voltage Vp2 is controlled to be the value A illustrated in FIG. 4, as illustrated in FIG. 5, in a range in which the NOx concentration is less than or equal to 2500 ppm, there is a linear relationship between the NOx concentration and the pump current Ip2a. By using this linear relationship, from the value of the pump current Ip2a, the NOx concentration can be calculated. The above-described first correspondence relationship 95 is determined in advance by experiment or the like as data representing such a linear relationship.

However, as indicated by FIG. 4, as the NOx concentration increases, the plateau region becomes narrower, and if the NOx concentration is too high, there is almost no plateau region. That is, the pump current Ip2a does not become the limiting current. For example, if the NOx concentration is higher than or equal to 3000 ppm in the example in FIG. 4, the pump current Ip2a does not become the limiting current. Thus, as illustrated in FIG. 5, if the NOx concentration exceeds 2500 ppm, the linear relationship between the NOx concentration and the pump current Ip2a is broken. Thus, if the NOx concentration exceeds 2500 ppm, the NOx concentration is not measured correctly by using the first measurement pump cell 41a. The range of the NOx concentration in which the pump current Ip2a becomes the limiting current changes depending on a first diffusion resistance $R_1$ that is a diffusion resistance of a route of the measurement-object gas from the outside of the sensor element 101 to the first measurement electrode 44. The higher the first diffusion resistance $R_1$, the less the amount of NOx flowing into the third internal cavity 61 per unit time becomes even if the NOx concentration is high. Thus, the first measurement pump cell 41a pumps out oxygen with ease to make oxygen derived from NOx substantially zero. Thus, as the first diffusion resistance $R_1$ is higher, the upper limit of the NOx concentration by which the pump current Ip2a becomes the limiting current is increased. In the example in FIG. 4, the upper limit of the NOx concentration by which the pump current Ip2a becomes the limiting current is 2500 ppm. In this embodiment, the value of the first diffusion resistance $R_1$ is mainly determined by a composite resistance of diffusion resistances of the first diffusion-rate-controlling section 11, the second diffusion-rate-controlling section 13, the third diffusion-rate-controlling section 30, and the fourth diffusion-rate-controlling section 60 that are present in series of a route of the measurement-object gas from the outside of the sensor element 101 to the first measurement electrode 44.

In contrast, as for the second measurement pump cell 41b, a diffusion resistance of a route of the measurement-object gas from the outside of the sensor element 101 to the second measurement electrode 45 is a second diffusion resistance $R_2$. In this embodiment, the measurement-object gas flow section is configured such that the measurement-object gas that has reached the third internal cavity 61, in which the first measurement electrode 44 is disposed, passes through the third internal cavity 61 and the fifth diffusion-rate-controlling section 62 in this order and reaches the fourth internal cavity 63 in which the second measurement electrode 45 is disposed. Thus, since the diffusion resistance of the fifth diffusion-rate-controlling section 62 that is connected in series to the fourth diffusion-rate-controlling section 60 is present, the second diffusion resistance $R_2$ is higher than the first diffusion resistance $R_1$. Thus, the second measurement pump cell 41b has a higher upper limit of the NOx concentration by which the pump current Ip2b becomes the limiting current than the first measurement pump cell 41a. In other words, even if the concentration of NOx in the measurement-object gas is higher in the second measurement pump cell 41b than in the first measurement pump cell 41a, the pump current can become the limiting current when oxygen is pumped out. In this embodiment, as illustrated in FIGS. 6 and 7, in the second measurement pump cell 41b, in a range in which the NOx concentration is less than or equal to 10000 ppm, the pump current Ip2b becomes the limiting current, there is a linear relationship between the NOx concentration and the pump current Ip2b. Thus, even in a range in which the NOx concentration is higher than 2500 ppm and lower than or equal to 10000 ppm and cannot be currently measured by the first measurement pump cell 41a, the second measurement pump cell 41b can accurately measure the NOx concentration and is suitable for detecting the NOx concentration if the NOx concentration is high. The above-described second correspondence relationship 96 is determined in advance by experiment or the like as data representing such a linear relationship illustrated in FIG. 7.

On the other hand, the value of the limiting current tends to decrease as the NOx concentration is lower. Thus, if the value of the limiting current is too small, the measurement accuracy is likely to decrease by being influenced by errors or the like. Thus, for example, as indicated by FIG. 7, in the second measurement pump cell 41b, if the NOx concentration is less than 2000 ppm, the pump current Ip2b becomes a small value that is less than 1 μA, and the measurement accuracy is likely to decrease. In contrast, the first measurement pump cell 41a can cause a comparatively high limiting current to flow even if the NOx concentration is lower than that in the second measurement pump cell 41b. For example, as indicated by FIG. 5, in the first measurement pump cell 41a, if the NOx concentration is greater than or equal to 500 ppm, a pump current Ip2a of higher than or equal to 1 μA can be caused to flow. Thus, even in a range in which the NOx concentration is higher than or equal to 500 ppm and lower than 2000 ppm and cannot be currently measured by the second measurement pump cell 41b, the first measurement pump cell 41a can accurately measure the NOx concentration and is suitable for detecting the NOx concentration if the NOx concentration is low.

From the above, the first measurement pump cell 41a is suitable for detecting the NOx concentration that is a comparatively low concentration, which is higher than or equal to 500 ppm and lower than or equal to 2500 ppm, whereas the second measurement pump cell 41b is suitable for detecting the NOx concentration that is a comparatively high concentration, which is higher than or equal to 2000 ppm and lower than or equal to 10000 ppm. Thus, by selectively using the first measurement pump cell 41a and the second measurement pump cell 41b, the sensor element 101 according to this embodiment can accurately detect the NOx concentration in a broad range from a low concentration to a high concentration (here, higher than or equal to 500 ppm and lower than or equal to 10000 ppm) compared with, for example, a sensor element including only one of the first measurement pump cell 41a and the second measurement pump cell 41b.

Note that the values of the NOx concentration and of the pump current illustrated in FIGS. 4 to 7 are examples, and by adjusting the first diffusion resistance $R_1$ and the second diffusion resistance $R_2$, the sensor element 101 can support the NOx concentration in any range. For example, by increasing the diffusion resistance of at least any of the first diffusion-rate-controlling section 11, the second diffusion-rate-controlling section 13, the third diffusion-rate-controlling section 30, and the fourth diffusion-rate-controlling section 60, both the first diffusion resistance $R_1$ and the second diffusion resistance $R_2$ can be increased. By increasing the diffusion resistance of the fifth diffusion-rate-controlling section 62, only the second diffusion resistance $R_2$ can be increased. Although each of the first to fifth diffusion-rate-controlling sections 11, 13, 30, 60, and 62 according to this embodiment is a slit, for example, by adjusting the area of a cross section of a flow line or the length of a flow line of the slit, the diffusion resistance can be adjusted. It is preferable to adjust the diffusion resistance of the first to fifth diffusion-rate-controlling sections 11, 13, 30, 60, and 62 such that the range of the NOx concentration (here, lower than or equal to 2500 ppm) in which the linear relationship between the NOx concentration and the pump current Ip2a exists in the first measurement pump cell 41a at least partly overlaps with the range of the NOx concentration (here, higher than or equal to 2000 ppm) corresponding to a range in which the value of the limiting current is not too small (e.g., the range of higher than or equal to 1 µA) in the second measurement pump cell 41b. The range $R_2/R_1$ may be greater than 1 and less than or equal to 100. The range $R_2/R_1$ can be calculated from the ratio of the limiting current between the first measurement pump cell 41a and the second measurement pump cell 41b. Specifically, first, by using a model gas having a NOx concentration that is known, the value of the pump current Ip2a (i.e., the pump current Ip2a on the above-described low concentration measurement mode) that flows when the first measurement pump cell 41a is controlled such that the pump current Ip2a becomes the limiting current is measured. Similarly, by using the same model gas, the value of the pump current Ip2b (i.e., the pump current Ip2b on the above-described high concentration measurement mode) that flows when the second measurement pump cell 41b is controlled such that the pump current Ip2b becomes the limiting current is measured. In addition, since the limiting current is in proportion to the reciprocal of the diffusion resistance, the ratio Ip2a/Ip2b of the limiting current is equal to the ratio $R_2/R_1$ of the diffusion resistance. Thus, the value of the ratio Ip2a/Ip2b based on the measured values is the value of the ratio $R_2/R_1$, and thereby the ratio $R_2/R_1$ can be calculated.

Figure 8:
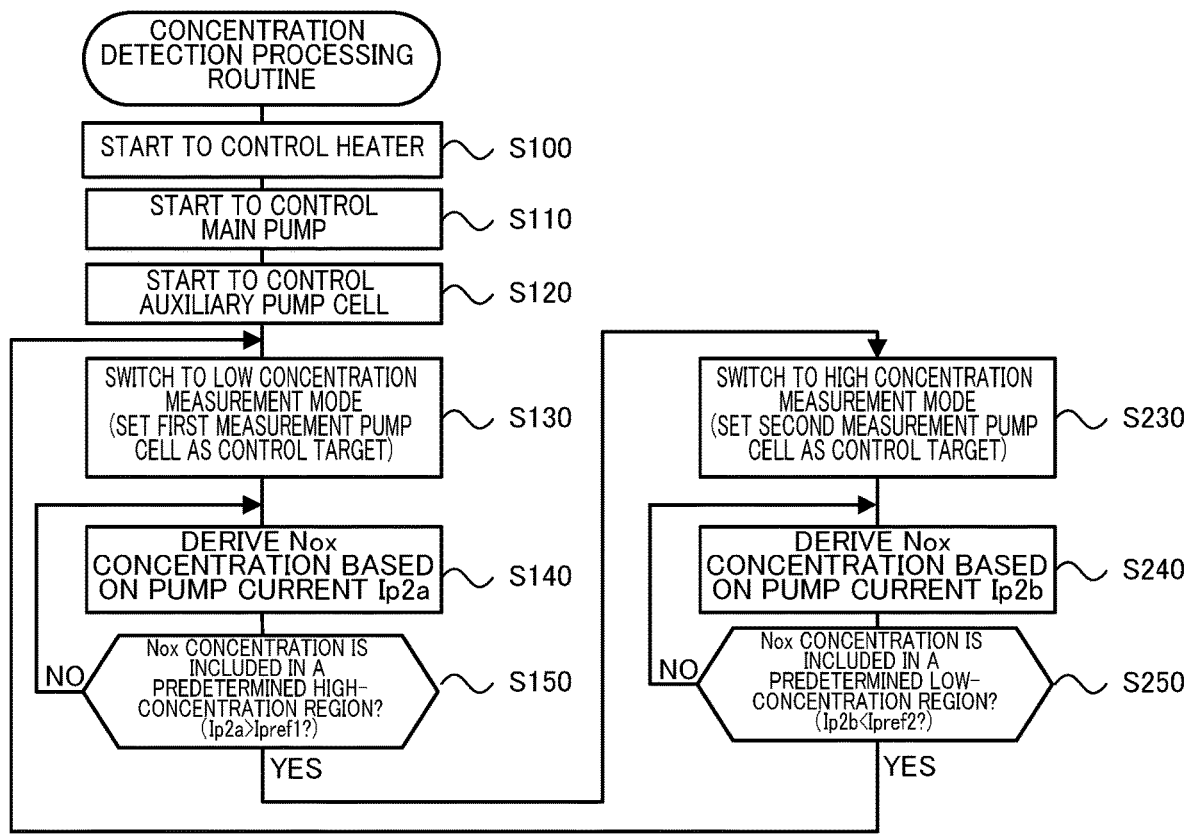
FIG. 8 is a flowchart illustrating an example of a concentration detection processing routine.

Now, an example in which the gas sensor 100 configured in the above manner is used will be described below. FIG. 8 is a flowchart illustrating an example of a concentration detection processing routine. This routine is stored in the storage unit 94 and starts, for example, upon the power of the control device 90 being turned on.

In response to start of the concentration detection processing routine, first, the CPU 92 of the control unit 91 applies power to the heater 72 and starts to control the heater 72 (step S100) and maintains the sensor element 101 at a temperature at which the solid electrolyte is active (e.g., 800° C.). Subsequently, the CPU 92 starts to control the main pump cell 21 (step S110) and also starts to control the auxiliary pump cell 50 (step S120). That is, the CPU 92 controls the main pump cell 21 by performing the above-described feedback control based on the target value Ip1* and the target value V0*, and controls the auxiliary pump cell 50 by performing the above-described feedback control based on the target value V1*. Any of steps S110 and S120 may be performed earlier, or steps S110 and S120 may be performed concurrently. Herein, the measurement-object gas passes from the gas inlet 10 through the first diffusion-rate-controlling section 11, the buffer space 12, the second diffusion-rate-controlling section 13, the first internal cavity 20, the third diffusion-rate-controlling section 30, the second internal cavity 40, and the fourth diffusion-rate-controlling section 60 in this order and reaches the third internal cavity 61. Then, the measurement-object gas is subjected to adjustment of the oxygen concentration within the first internal cavity 20 and the second internal cavity 40 and reaches the third internal cavity 61 and the fourth internal cavity 63 in a downstream side thereof.

Subsequently, the CPU 92 switches to the low concentration measurement mode (step S130). Specifically, the CPU 92 switches the switch 85 so as to be able to receive the voltage V2a from the first-measurement-pump-controlling oxygen-partial-pressure detection sensor cell 82a, and switches the switch 86 to set the first measurement pump cell 41a as a control target. Thus, the CPU 92 performs the above-described feedback control based on the target value V2* to control the first measurement pump cell 41a such that the pump current Ip2a becomes the limiting current. In this low concentration measurement mode state, the second measurement pump cell 41b does not cause the pump current Ip2b to flow. That is, the second measurement pump cell 41b does not pump out oxygen in the fourth internal cavity 63. Subsequently, based on the pump current Ip2a and the first correspondence relationship 95, the CPU 92 derives the NOx concentration in the measurement-object gas (step S140). In the above manner, the NOx concentration is measured on the low concentration measurement mode.

After step S140, based on the pump current Ip2a, the CPU 92 determines whether the NOx concentration in the measurement-object gas is included in a predetermined high-concentration region (step S150). Specifically, the CPU 92 determines whether the pump current Ip2a exceeds a predetermined threshold Ipref1. The threshold Ipref1 is determined in advance as the upper limit value of a range in which the pump current Ip2a is low and the NOx concentration can be regarded as a low concentration, that is, a range that can be regarded as being suitable for measurement on the low concentration measurement mode. The threshold Ipref1 is set to, for example, the upper limit (here, 5 µA) of the range in which the linear relationship between the NOx concentration and the pump current Ip2a exists in the first measurement pump cell 41a, or a value that is a little smaller than the upper limit by providing a margin. In this embodiment, the threshold Ipref1 is set to the value 4.8 µA (value corresponding to the NOx concentration of 2400 ppm). If the pump current Ip2a is lower than or equal to the threshold Ipref1 in step S150, the CPU 92 performs processing in and after step S140. That is, based on the pump current Ip2a, if the NOx concentration is not included in the high concentration region, that is, if the NOx concentration can be regarded as a low concentration, the CPU 92 continuously measures the NOx concentration on the low concentration measurement mode.

On the other hand, if the pump current Ip2a exceeds the threshold Ipref1 in step S150, the CPU 92 switches to the high concentration measurement mode (step S230). Specifically, the CPU 92 switches the switch 85 so as to be able to receive the voltage V2b from the second-measurement-pump-controlling oxygen-partial-pressure detection sensor cell 82b, and switches the switch 86 to set the second measurement pump cell 41b as a control target. Thus, the CPU 92 performs the above-described feedback control based on the target value V2* to control the second measurement pump cell 41b such that the pump current Ip2b becomes the limiting current. In this high concentration measurement mode state, the first measurement pump cell 41a does not cause the pump current Ip2a to flow. That is, the first measurement pump cell 41a does not pump out oxygen in the third internal cavity 61. Subsequently, based on the pump current Ip2b and the second correspondence relationship 96, the CPU 92 derives the NOx concentration in the measurement-object gas (step S240). In the above manner, the NOx concentration is measured on the high concentration measurement mode.

After step S240, based on the pump current Ip2b, the CPU 92 determines whether the NOx concentration in the measurement-object gas is included in a predetermined low-concentration region (step S250). Specifically, the CPU 92 determines whether the pump current Ip2b is less than a predetermined threshold Ipref2. The threshold Ipref2 is determined in advance as the lower limit value of a range in which the pump current Ip2b is high and the NOx concentration can be regarded as a high concentration, that is, a range that can be regarded as being suitable for measurement on the high concentration measurement mode. The threshold Ipref2 is set to, for example, the lower limit (here, 1 µA) of the range of the pump current Ip2b in which a decrease in measurement accuracy caused by the influence of errors or the like in the second measurement pump cell 41b is not a problem, or a value that is a little larger than the lower limit by providing a margin. In addition, to prevent frequent switching between the low concentration measurement mode and the high concentration measurement mode, the threshold Ipref2 is preferably set such that the NOx concentration corresponding to the threshold Ipref2 has a smaller value than the NOx concentration corresponding to the threshold Ipref1. That is, it is preferable to provide hysteresis between the NOx concentration corresponding to the threshold Ipref1 and the NOx concentration corresponding to the threshold Ipref2. In this embodiment, considering these, the threshold Ipref2 is set to the value 1.05 µA (value corresponding to the NOx concentration of 2100 ppm). If the pump current Ip2b is higher than or equal to the threshold Ipref2 in step S250, the CPU 92 performs processing in and after step S240. That is, based on the pump current Ip2b, if the NOx concentration is not included in the low concentration region, that is, if the NOx concentration can be regarded as a high concentration, the CPU 92 continuously measures the NOx concentration on the high concentration measurement mode. On the other hand, if the pump current Ip2b is lower than the threshold Ipref2 in step S250, the CPU 92 performs processing in and after step S130. That is, the CPU 92 switches to the low concentration measurement mode and measures the NOx concentration.

In the above manner, based on the pump currents Ip2a and Ip2b, the CPU 92 determines whether to employ the low concentration measurement mode or the high concentration measurement mode to detect the NOx concentration. Thus, it is possible to appropriately switch between the low concentration measurement mode and the high concentration measurement mode and to accurately detect the specific gas concentration in a broad range from the lower concentration to the high concentration (e.g., greater than or equal to 500 ppm and less than or equal to 10000 ppm in this embodiment).

Note that the value of the pump current Ip2a may be unstable immediately after switching in step S130 from the high concentration measurement mode to the low concentration measurement mode. Thus, the CPU 92 may perform step S140 when a predetermined waiting time elapses. The same applies to the time immediately after step S230.

Since the measurement-object gas passes through the third internal cavity 61 before reaching the fourth internal cavity 63, on the high concentration measurement mode, NOx may be reduced to produce oxygen not only around the second measurement electrode 45 but also around the first measurement electrode 44. However, since the first measurement pump cell 41a does not pump out oxygen on the high concentration measurement mode, the second measurement pump cell 41b pumps out oxygen produced around the first measurement electrode 44 and around the second measurement electrode 45. Thus, even if oxygen produced around the first measurement electrode 44 is present, as a result, the amount of oxygen produced from NOx is in proportion to the pump current Ip2b. Thus, on the high concentration measurement mode, the control unit 91 can calculate the NOx concentration based on the pump current Ip2b without any problem.

Note that, on the low concentration measurement mode, before the measurement-object gas reaches the fourth internal cavity 63, NOx is reduced to produce oxygen around the first measurement electrode 44 in the third internal cavity 61, and the first measurement pump cell 41a pumps out the oxygen. Thus, basically, NOx in the measurement-object gas does not reach the second measurement electrode 45. Even if NOx reaches the second measurement electrode 45 and is reduced around the second measurement electrode 45 to produce oxygen, the second measurement pump cell 41b does not pump out oxygen on the low concentration measurement mode. In addition, since the third internal cavity 61 has a lower oxygen concentration than the fourth internal cavity 63 by the operation of the first measurement pump cell 41a, the oxygen produced around the second measurement electrode 45 diffuses to move toward the third internal cavity 61. Thus, even if oxygen produced around the second measurement electrode 45 is present, the first measurement pump cell 41a pumps out the oxygen, and, as a result, the amount of oxygen produced from NOx is in proportion to the pump current Ip2a. Thus, on the low concentration measurement mode, the control unit 91 can calculate the NOx concentration based on the pump current Ip2a without any problem. Note that, on the low concentration measurement mode, the switch 85 may be omitted, and the control unit 91 may acquire both the voltage V2a and the voltage V2b and may control the first measurement pump cell 41a such that the average of the voltage V2a and the voltage V2b becomes a target value. In this manner, even if oxygen produced not only around the first measurement electrode 44 but also around the second measurement electrode 45 is present, the control device 90 can control the first measurement pump cell 41a taking into account the amount of the oxygen. Also in this case, on the low concentration measurement mode, the control unit 91 can calculate the NOx concentration based on the pump current Ip2a without any problem.

Now, correspondence relationships between structural elements in this embodiment and structural elements in the present invention will be clearly described. The first substrate layer 1, the second substrate layer 2, the third substrate layer 3, the first solid electrolyte layer 4, the spacer layer 5, and the second solid electrolyte layer 6 in this embodiment corresponds to an element body in the present invention; the first internal cavity 20 and the second internal cavity 40 correspond to the oxygen concentration adjustment chamber; the main pump cell 21 and the auxiliary pump cell 50 correspond to the adjustment pump cell; the third internal cavity 61 corresponds to the first measurement chamber; the first measurement electrode 44 corresponds to a first measurement electrode; the first measurement pump cell 41a corresponds to a first measurement pump cell; the fourth internal cavity 63 corresponds to the second measurement chamber; the second measurement electrode 45 corresponds to a second measurement electrode; the second measurement pump cell 41b corresponds to a second measurement pump cell; the outer pump electrode 23 corresponds to a first outer measurement electrode and a second outer measurement electrode; the fourth diffusion-rate-controlling section 60 corresponds to the first measurement-electrode diffusion-rate-controlling section; and the fifth diffusion-rate-controlling section 62 corresponds to the second measurement-electrode diffusion-rate-controlling section. In addition, the control device 90 corresponds to a specific gas concentration detection device. The first-measurement-pump-controlling oxygen-partial-pressure detection sensor cell 82a corresponds to a first measurement voltage detection device, and the second-measurement-pump-controlling oxygen-partial-pressure detection sensor cell 82b corresponds to a second measurement voltage detection device.

In the gas sensor 100 according to this embodiment that has been described above in detail, the sensor element 101 includes the first measurement pump cell 41a and the second measurement pump cell 41b. In addition, since the fourth diffusion-rate-controlling section 60 and the fifth diffusion-rate-controlling section 62 are disposed in series, the sensor element 101 is configured such that the second diffusion resistance $R_2$, which is a diffusion resistance of a route of the measurement-object gas from the outside of the sensor element 101 to the second measurement electrode 45, is higher than the first diffusion resistance Ru which is a diffusion resistance of a route of the measurement-object gas from the outside of the sensor element 101 to the first measurement electrode 44. Thus, the first measurement pump cell 41a is suitable for detecting the NOx concentration if the NOx concentration is low, and the second measurement pump cell 41b is suitable for detecting the NOx concentration if the NOx concentration is high. By selectively using the first measurement pump cell 41a and the second measurement pump cell 41b, the sensor element 101 can accurately detect the NOx concentration in a broad range. Specifically, on the low concentration measurement mode, based on the value of the pump current Ip2a that flows in the first measurement pump cell 41a, the control device 90 detects the NOx concentration in the measurement-object gas, thereby accurately detecting the NOx concentration that is a low concentration. In addition, on the high concentration measurement mode, based on the value of the pump current Ip2b that flows in the second measurement pump cell 41b, the control device 90 detects the NOx concentration in the measurement-object gas, thereby accurately detecting the NOx concentration that is a high concentration.

Furthermore, on the low concentration measurement mode, if the control device 90 determines, based on the pump current Ip2a, that the NOx concentration in the measurement-object gas is included in the predetermined high-concentration range, the control device 90 switches to the high concentration measurement mode; on the high concentration measurement mode, if the control device 90 determines, based on the pump current Ip2b, that the NOx concentration in the measurement-object gas is included in the predetermined low-concentration range, the control device 90 switches to the low concentration measurement mode. Thus, based on the pump currents Ip2a and Ip2b, the control device 90 can appropriately switch between the low concentration measurement mode and the high concentration measurement mode.

The present invention is not limited to the above-described embodiment and may be, of course, implemented in various modes within the technical scope of the present invention.

Figure 9:
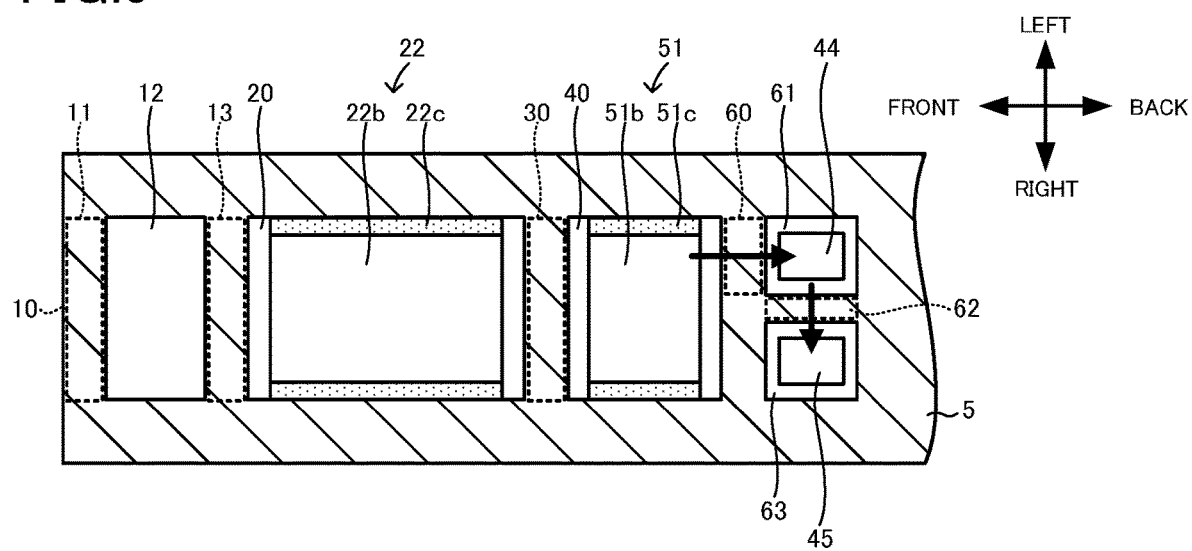
FIG. 9 is a schematic sectional view of a measurement-object gas flow section in a modification.

For example, in the above-described embodiment, the fourth diffusion-rate-controlling section 60, the third internal cavity 61, the fifth diffusion-rate-controlling section 62, and the fourth internal cavity 63 are disposed in this order in the front-to-back direction. However, the order is not limited to this as long as the fourth diffusion-rate-controlling section 60 and the fifth diffusion-rate-controlling section 62 are disposed in series. For example, as illustrated in FIG. 9, the fifth diffusion-rate-controlling section 62 and the fourth internal cavity 63 may be disposed in this order in the horizontal direction relative to the third internal cavity 61. Also in this case, the diffusion resistance $R_2$ is higher than the diffusion resistance $R_1$. Thus, as in the above-described embodiment, the second measurement pump cell 41b is suitable for detecting the NOx concentration that is higher than that in the first measurement pump cell 41a. Note that, in FIG. 9, the width of each of the third internal cavity 61 and the fourth internal cavity 63 in the horizontal direction is less than half of that in FIG. 2. Compared with the main pump cell 21 and the auxiliary pump cell 50, the first measurement pump cell 41a and the second measurement pump cell 41b pump out a small amount of oxygen. Thus, even if the capacity of the third internal cavity 61 and the fourth internal cavity 63 are reduced in the above manner and the first measurement electrode 44 and the second measurement electrode 45 are smaller, the amount of oxygen pumped out by the first measurement pump cell 41a and the second measurement pump cell 41b is unlikely to be insufficient.

Figure 10:
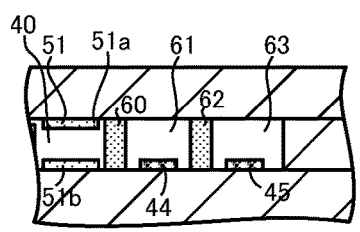
FIG. 10 is a schematic sectional view of a fourth diffusion-rate-controlling section 60 and a fifth diffusion-rate-controlling section 62 in a modification.

In the above-described embodiment, the fourth diffusion-rate-controlling section 60 and the fifth diffusion-rate-controlling section 62 are configured as slit-like gaps. However, the configuration is not limited to this. For example, as illustrated in FIG. 10, the fourth diffusion-rate-controlling section 60 and the fifth diffusion-rate-controlling section 62 may be formed of porous ceramics (e.g., alumina ($Al_2O_3$)). In this case, the diffusion resistances can be adjusted by adjusting the porosity, the pore size, and the like of each of the fourth diffusion-rate-controlling section 60 and the fifth diffusion-rate-controlling section 62. Similarly, the first to third diffusion-rate-controlling sections 11, 13, and 30 may also be formed of porous bodies.

Figure 11:
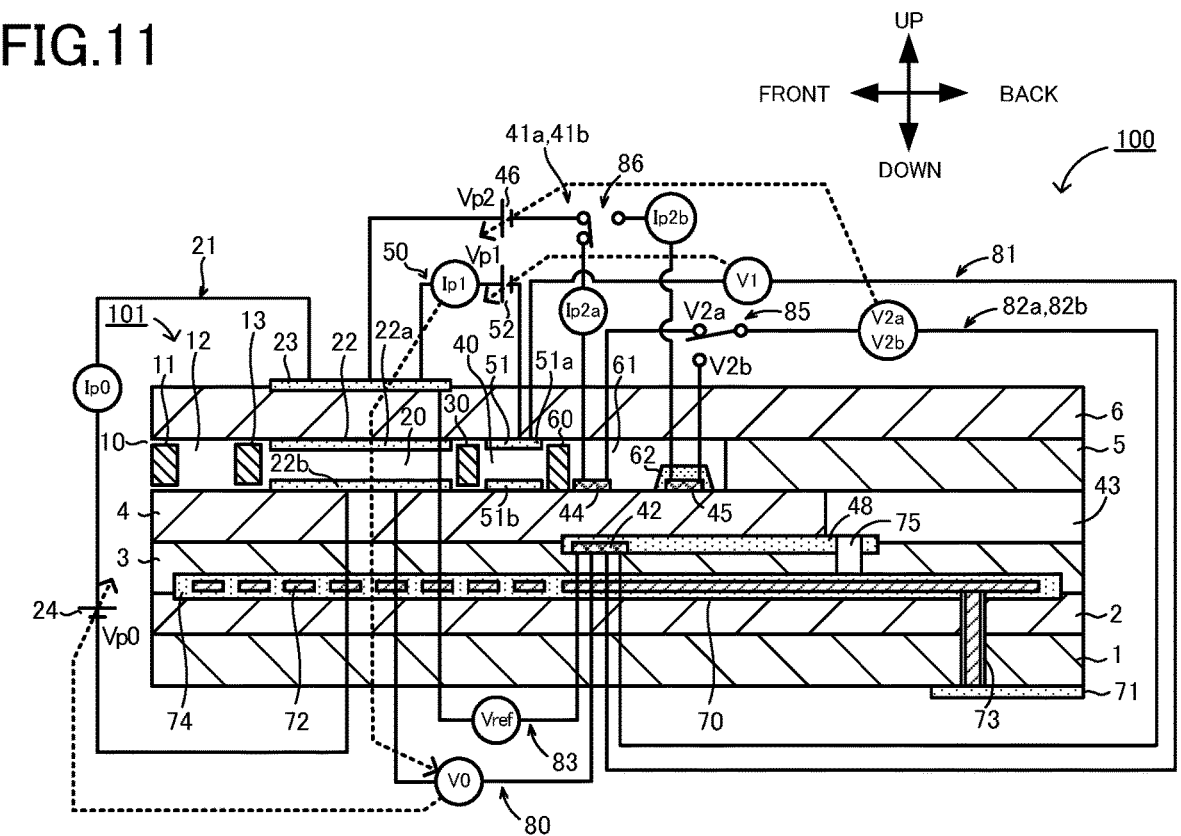
FIG. 11 is a schematic sectional view of the fifth diffusion-rate-controlling section 62 in a modification.

If at least one of the fourth diffusion-rate-controlling section 60 and the fifth diffusion-rate-controlling section 62 is a porous body, the porous body may cover a measurement electrode. For example, as illustrated in FIG. 11, the fifth diffusion-rate-controlling section 62 may cover the second measurement electrode 45. In FIG. 11, the fourth internal cavity 63 is not present, and the fifth diffusion-rate-controlling section 62 is disposed within the third internal cavity 61. In this case, the inside of the fifth diffusion-rate-controlling section 62, in other words, a portion around the second measurement electrode 45, serves as the second measurement chamber as well as the fourth internal cavity 63 in the above-described embodiment. In the case in FIG. 11, also, the measurement-object gas flow section is configured such that the measurement-object gas passes through the first measurement-electrode diffusion-rate-controlling section (here, the fourth diffusion-rate-controlling section 60), the first measurement chamber (here, the third internal cavity 61), and the second measurement-electrode diffusion-rate-controlling section (here, the fifth diffusion-rate-controlling section 62) in this order and reaches the second measurement chamber. That is, the fourth diffusion-rate-controlling section 60 and the fifth diffusion-rate-controlling section 62 are disposed in series, and thus, as in the above-described embodiment, the second measurement pump cell 41b is suitable for detecting the NOx concentration that is higher than that in the first measurement pump cell 41a.

Figure 12:
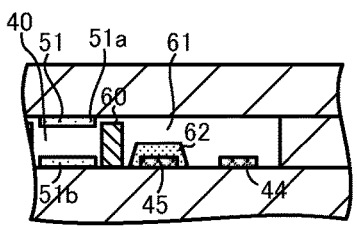
FIG. 12 is a schematic sectional view of the fifth diffusion-rate-controlling section 62 and a second measurement electrode 45 in a modification.
Figure 13:
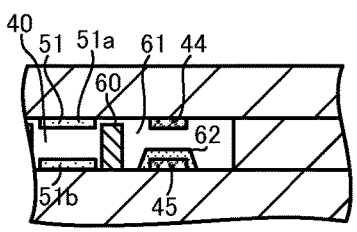
FIG. 13 is a schematic sectional view of the fifth diffusion-rate-controlling section 62 and the second measurement electrode 45 in a modification.

In addition, in the example in FIG. 11, since the first measurement electrode 44 and the set of the fifth diffusion-rate-controlling section 62 and the second measurement electrode 45 are disposed in the third internal cavity 61 together, these positions in the front-to-back direction may be switched as illustrated in FIG. 12. Alternatively, the first measurement electrode 44 and the set of the fifth diffusion-rate-controlling section 62 and the second measurement electrode 45 may be disposed in an upper portion and a lower portion within the third internal cavity 61 as illustrated in FIG. 13. In the embodiments in FIGS. 12 and 13, the second measurement pump cell 41b is suitable for detecting the NOx concentration that is higher than that in the first measurement pump cell 41a.

In the above-described embodiment, the control unit 91 selectively receives the voltage V2a and the voltage V2b by using the switch 85. However, the switch 85 may be omitted, and the voltage V2a and the voltage V2b may be independently input. In addition, the control unit 91 selectively switches whether the control target is any of the first measurement pump cell 41a and the second measurement pump cell 41b by using the switch 86. However, the switch 86 may be omitted, and each of the first measurement pump cell 41a and the second measurement pump cell 41b may be independently controlled. In this case, two variable power sources 46 may be provided, and either one may be used for controlling the first measurement pump cell 41a and the other one may be used for controlling the second measurement pump cell 41b.

In the above-described embodiment, the sensor element 101 includes two measurement pump cells, which are the first measurement pump cell 41a and the second measurement pump cell 41b. However, the sensor element 101 may also include three or more measurement pump cells in total. For example, the sensor element 101 may include a third measurement-electrode diffusion-rate-controlling section and a third measurement chamber in this order further on a downstream side of the fourth internal cavity 63, and a third measurement electrode may be disposed in the third measurement chamber. That is, the following general expression is possible. When n is an integer of greater than or equal to 3, the sensor element 101 may include first to n-th measurement pump cells including the first measurement pump cell 41a and the second measurement pump cell 41b. When p is an integer from 3 to n, a p-th measurement pump cell may include a p-th measurement electrode and a p-th outer measurement electrode and may be configured to pump out oxygen produced in a p-th measurement chamber from the specific gas, the p-th measurement electrode being disposed in the p-th measurement chamber provided on a downstream side of the oxygen concentration adjustment chamber (the first internal cavity 20 and the second internal cavity 40 in the above-described embodiment) in the measurement-object gas flow section, the p-th outer measurement electrode being provided outside the element body (the layers 1 to 6 in the above-described embodiment) so as to contact with the measurement-object gas. The measurement-object-gas flow section may be configured such that the measurement-object gas passes through a (p−1)-th measurement chamber and a p-th measurement-electrode diffusion-rate-controlling section in this order and reaches the p-th measurement chamber. Thus, the first to n-th measurement-electrode diffusion-rate-controlling sections are disposed in this order in series. Thus, when a diffusion resistance of a route of the measurement-object gas from the outside of the sensor element 101 to the p-th measurement electrode is a p-th diffusion resistance $R_p$, the p-th diffusion resistance $R_p$ is higher than a (p−1)-th diffusion resistance $R_{p-1}$, that is, $R_1 < R_2 < \ldots R_{n-1} < R_n$ is satisfied. Thus, by selectively using the first to n-th measurement pump cells, sensor element 101 can accurately detect the specific gas concentration in a broader range (detection range of the specific gas concentration) compared with a sensor element 101 including only the first and second measurement pump cells 41a and 41b. For example, n may be less than or equal to 5.

If the NOx concentration is measured by using the sensor element 101 including three or more measurement pump cells, as in the above-described embodiment, the control device 90 may selectively employ a plurality of modes. Specifically, the control device 90 has first to n-th measurement modes, and, if q is an integer from 1 to n, a q-th measurement mode may be a mode on which a q-th measurement pump cell is controlled such that a pump current that flows in the q-th measurement pump cell becomes the limiting current, and, based on the value of the pump current, the specific gas concentration in the measurement-object gas is detected. In this case, the gas sensor 100 may include, not only the first- and second-measurement-pump-controlling oxygen-partial-pressure detection sensor cell 82a and 82b, but also third- to nth-measurement-pump-controlling oxygen-partial-pressure detection sensor cells, to correspond to the respective first to n-th measurement pump cells. That is, when q is an integer from 1 to n, the gas sensor 100 may include a q-th measurement voltage detection device that detects a q-th measurement voltage between the reference electrode 42 and a q-th measurement electrode. In addition, on the q-th measurement mode, the control device 90 may control the q-th measurement pump cell based on the q-th measurement voltage. For example, the control device 90 may perform feedback control of a variable power source that applies voltage to the q-th measurement pump cell such that the q-th measurement voltage becomes a target value, and may control the pump current that flows in the q-th measurement pump cell.

The control device 90 may switch between the first to n-th measurement modes as follows, for example. That is, when r is an integer from 1 to n, based on a pump current that flows in an r-th measurement pump cell on an r-th measurement mode, if it is determined that the specific gas concentration in the measurement-object gas exceeds the upper limit value of an r-th region that is a region of a predetermined specific gas concentration set corresponding to the r-th measurement mode, the control device 90 may change the measurement mode to a (r+1)-th measurement mode (except when r=n). Similarly, based on the pump current that flows in the r-th measurement pump cell on the r-th measurement mode, if it is determined that the specific gas concentration in the measurement-object gas is lower than the lower limit value of the r-th region set corresponding to the r-th measurement mode, the control device 90 may change the measurement mode to a (r−1)-th measurement mode (except when r=1). That is, for each of the first to n-th measurement modes, the region of the specific gas concentration suitable for the measurement mode (first to n-th regions) are set in advance (stored in the storage unit 94, for example). In addition, the control device 90 may determine, based on the pump current, whether the current specific gas concentration exceeds a region suitable for the current measurement mode or falls below the region, and, in accordance with the determination result, the control device 90 may switch from the r-th measurement mode to the adjacent (r+1)-th measurement mode or the adjacent (r−1)-th measurement mode. In this case, the control device 90 switches the measurement mode stage by stage. In addition, the ranges of the first to n-th regions in this case may party overlap between adjacent regions. The first to n-th regions may be determined as a range of the specific gas concentration or may be determined as a range of numerical values (e.g., pump current) that can be regarded as the range of the specific gas concentration.

Alternatively, the control device 90 may allow switching of the measurement mode by two or more stages at a time, such as switching of the measurement mode from the r-th measurement mode to a (r+2)-th measurement mode. For example, if the above-described first to n-th regions are set in advance, based on the pump current that flows in the r-th measurement pump cell on the r-th measurement mode, the control device 90 may determine whether the specific gas concentration in the measurement-object gas is included in an x-th region that is any of the first to n-th regions other than the r region (x is an integer of greater than or equal to 1 and less than or equal to n and other than r), and, if it is determined that the specific gas concentration is included in the x-th region, the control device 90 may change the measurement mode to an x-th measurement mode. In the above manner, for example, if the concentration of the measurement-object gas abruptly and largely varies, the measurement mode can be changed to an appropriate measurement mode in a shorter time than in a case in which the measurement mode is switched stage by stage. The ranges of the first to n-th regions in this case preferably do not overlap between adjacent regions (e.g., the ranges are continuous).

In the above-described embodiment, "greater than 1 and less than or equal to 100" is illustrated as the numerical value range of the ratio $R_2/R_1$. If the sensor element 101 includes three or more measurement pump cells, also, substantially the same numerical value range may be satisfied. Specifically, as for the above-described first to n-th diffusion resistances $R_1$ to $R_n$, when k is an integer from 1 to n−1, a ratio $R_{k+1}/R_k$ between a k-th diffusion resistance $R_k$ (a diffusion resistance of a route of the measurement-object gas from an outside to a k-th measurement electrode) and a (k+1)-th diffusion resistance $R_{k+1}$ (a diffusion resistance of a route of the measurement-object gas from the outside to a (k+1)-th measurement electrode) may be greater than 1 and less than or equal to 100. That is, for each of the first to n-th measurement electrodes, the ratio of the diffusion resistance from the outside to a measurement electrode between adjacent measurement electrodes may be greater than 1 and less than or equal to 100. The value of the ratio $R_{k+1}/R_k$ can be calculated by substantially the same method for the above-described ratio $R_2/R_1$. Note that the expression "the ratio $R_{k+1}/R_k$ is greater than 1 and less than or equal to 100" means that each of the values of ratios $R_2/R_1$, $R_3/R_2$, . . . , and $R_n/R_{n-1}$ is a value in the range of greater than 1 and less than or equal to 100, and all of these ratios are not necessarily the same value.

In the above-described embodiment, after step S120, first, the CPU 92 switches to the low concentration measurement mode in step S130. However, after step S120, first, the CPU 92 may switch to the high concentration measurement mode in step S230.

In the above-described embodiment, based on the pump currents Ip2a and Ip2b, the CPU 92 switches between the low concentration measurement mode and the high concentration measurement mode. However, switching is not limited to this. For example, the CPU 92 may switch based on a signal from another device such as an engine ECU.

In the above-described embodiment, the sensor element 101 may include a porous protective layer (e.g., porous ceramics such as alumina ($Al_2O_3$)) covering a portion around a forward end of the element body. Thus, the porous protective layer can, for example, suppress thermal shock on the element body caused by attachment of moisture in the measurement-object gas and can suppress a crack in the element body. If the porous protective layer covers the gas inlet 10, the diffusion resistance of the porous protective layer also influences the values of the first diffusion resistance $R_1$ and the second diffusion resistance $R_2$ described above.

In the above-described embodiment, the inner pump electrode 22 is a cermet electrode of Pt and $ZrO_2$ containing Au at 1%. However, the inner pump electrode 22 is not limited to this. The inner pump electrode 22 may include a noble metal having catalytic activity (e.g., at least any of Pt, Rh, Ir, Ru, and Pd) and a noble metal having a catalytic activity suppressing function of suppressing the catalytic activity with respect to a specific gas of the noble metal having catalytic activity (e.g., Au). The auxiliary pump electrode 51 may also include a noble metal having catalytic activity and a noble metal having a catalytic activity suppressing function as well as the inner pump electrode 22. Each of the outer pump electrode 23, the reference electrode 42, the first measurement electrode 44, and the second measurement electrode 45 may include the above-described noble metal having catalytic activity. Each of the electrodes 22, 23, 42, 44, 45, and 51 is preferably a cermet containing a noble metal and oxygen-ion-conductive oxide (e.g., $ZrO_2$), but one or more of these electrodes is not necessarily a cermet. Each of the electrodes 22, 23, 42, 44, 45, and 51 is preferably a porous body, but one or more of these electrodes is not necessarily a porous body.

In the above-described embodiment, the gas sensor 100 detects the NOx concentration in the measurement-object gas. However, the gas sensor 100 is not limited to this as long as the gas sensor 100 is a limiting-current gas sensor that detects a specific gas concentration in the measurement-object gas. For example, the specific gas concentration may be, other than the NOx concentration, the concentration of another oxide. If the specific gas is oxide, as in the above-described embodiment, oxygen is produced when the specific gas itself is reduced in the third internal cavity 61 and the fourth internal cavity 63, and thus, detection values in accordance with the oxygen (e.g., the pump currents Ip2a and Ip2b) are acquired by using the first measurement pump cell 41a and the second measurement pump cell 41b, and the specific gas concentration can be detected. Alternatively, the specific gas may also be non-oxide, such as ammonia. If the specific gas is non-oxide, by converting the specific gas into oxide (e.g., if the specific gas is ammonia, by converting ammonia into NO), oxygen is produced when the converted gas is reduced in the third internal cavity 61 and the fourth internal cavity 63. Thus, the specific gas concentration can be detected as in a case in which the specific gas is oxide.

The specific gas can be converted into oxide by, for example, at least one of the inner pump electrode 22 and the auxiliary pump electrode 51 functioning as a catalyst.

Alternatively, the specific gas may be oxygen, and the gas sensor 100 may detect an oxygen concentration as the specific gas concentration in the measurement-object gas. If the control device 90 controls the sensor element 101 such that the pump currents Ip2a and Ip2b that flow in the first and second measurement pump cells 41a and 41b become limiting currents while not adjusting the oxygen concentration in the first internal cavity 20 and the second internal cavity 40 in the sensor element 101, the pump currents Ip2a and Ip2b become values in accordance with the oxygen concentration in the measurement-object gas. Thus, based on the pump currents Ip2a and Ip2b, the control device 90 can detect the oxygen concentration. For example, the control device 90 may control the sensor element 101 to perform the concentration detection processing routine in substantially the same manner as that in the above-described embodiment except that the main pump cell 21 and the auxiliary pump cell 50 are not operated. In addition, the control device 90 may control the first and second measurement pump cells 41a and 41b such that each of the pump currents Ip2a and Ip2b becomes the limiting current, and does not necessarily perform, for example, the above-described feedback control such that the voltages V2a and V2b become the target value V2*. For example, the value of the voltage Vp2 by which the pump current Ip2a becomes the limiting current on the low concentration measurement mode may be determined in advance, and the control device 90 may control the variable power source 46 to apply the voltage Vp2 of the value on the low concentration measurement mode. Similarly, the value of the voltage Vp2 by which the pump current Ip2b becomes the limiting current on the high concentration measurement mode may be determined in advance. If the gas sensor 100 detects the oxygen concentration as the specific gas concentration, as well as the inner pump electrode 22 and the auxiliary pump electrode 51, the first measurement electrode 44 and the second measurement electrode 45 are preferably formed of a material whose reduction ability for NOx components in the measurement-object gas is decreased. For example, each of the first measurement electrode 44 and the second measurement electrode 45 may contain the above-described noble metal having the catalytic activity suppressing function in addition to the above-described noble metal having catalytic activity. Note that, out of the first measurement electrode 44 and the second measurement electrode 45, the second measurement electrode 45 located on a downstream side in the measurement-object gas flow section is used to detect the oxygen concentration if oxygen has a high concentration, and thus, even if the NOx components are reduced, the influence on the oxygen concentration is low. Thus, the second measurement electrode 45 does not necessarily contain, for example, the above-described noble metal having the catalytic activity suppressing function. If the oxygen concentration in a measurement-object gas that does not include oxide such as NOx is to be measured, both the first measurement electrode 44 and the second measurement electrode 45 do not necessarily contain the noble metal having the catalytic activity suppressing function.

Figure 14:
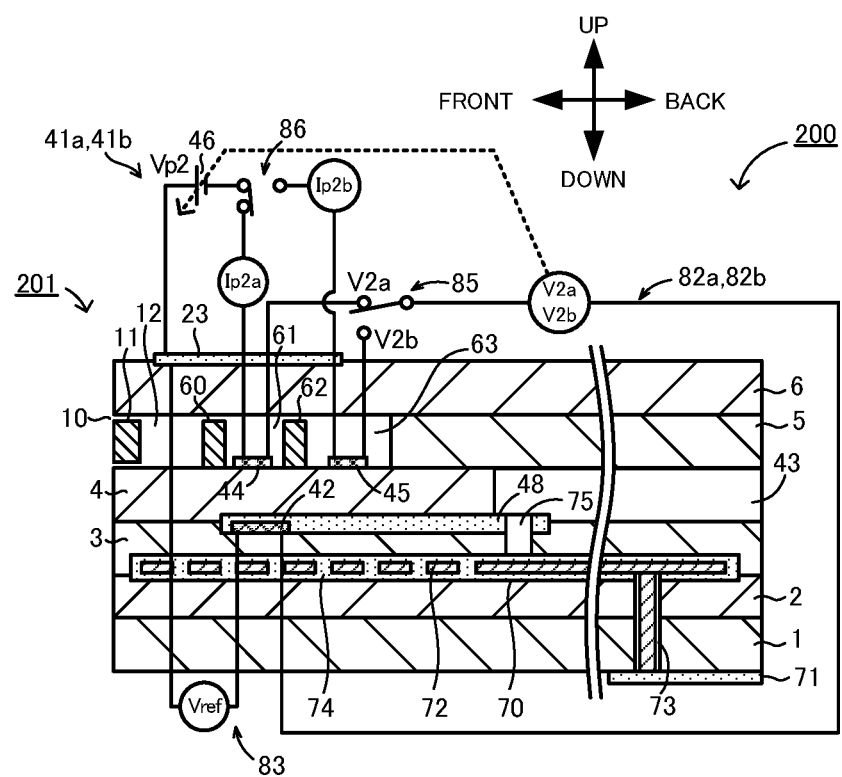
FIG. 14 is a schematic sectional view schematically illustrating an example of the configuration of a gas sensor 200 according to a modification.

If the gas sensor 100 detects the oxygen concentration as the specific gas concentration in the measurement-object gas, the gas sensor 100 does not necessarily include the adjustment pump cell and the oxygen concentration adjustment chamber. FIG. 14 is a schematic sectional view schematically illustrating an example of the configuration of a gas sensor 200 according to a modification. In FIG. 14, the same structural elements as those in the above-described embodiment are denoted by the same reference numerals. In a sensor element 201 of the gas sensor 200, the measurement-object gas flow section does not include the configuration corresponding to the oxygen concentration adjustment chamber, that is, the first internal cavity 20 and the second internal cavity 40 in FIG. 1, and does not include the second diffusion-rate-controlling section 13 and the third diffusion-rate-controlling section 30 either. Thus, the measurement-object gas that passes through the first diffusion-rate-controlling section 11 into the buffer space 12 directly passes through the fourth diffusion-rate-controlling section 60 provided in a downstream of the buffer space 12 and reaches the third internal cavity 61. In the gas sensor 200, also, the pump currents Ip2a and Ip2b flowing in the first and second measurement pump cells 41a and 41b become values in accordance with the oxygen concentration in the measurement-object gas, and thus, the oxygen concentration can be detected based on the pump currents Ip2a and Ip2b. In the sensor element 201, the buffer space 12 and the fourth diffusion-rate-controlling section 60 may be omitted. In this case, the first diffusion-rate-controlling section 11 corresponds to the first measurement-electrode diffusion-rate-controlling section. Furthermore, if the opening area of the gas inlet 10 is so small that the gas inlet 10 functions as a diffusion-rate-controlling section, a slit-like gap like the first diffusion-rate-controlling section 11 may be omitted. In this case, the gas inlet 10 corresponds to the first measurement-electrode diffusion-rate-controlling section.

If the gas sensor 100 detects the oxygen concentration as the specific gas concentration in the measurement-object gas, also, the above-described various embodiments or configurations for measuring the NOx concentration may be employed. For example, the sensor element 101 may include the above-described first to n-th measurement pump cells, and the control device 90 may have the first to n-th measurement modes. For example, if the measurement-object gas is exhaust gas of the internal combustion engine, the oxygen concentration in the measurement-object gas may change in a boarder range than the NOx concentration (e.g., range from less than 1 ppm to several percent). Thus, if the gas sensor 100 detects the oxygen concentration, it is effective that the sensor element 101 includes three or more measurement pump cells in total to increase the range in which the oxygen concentration can be accurately detected (detection range of the oxygen concentration).

In the above-described embodiment, the element body of the sensor element 101 is the layered body having the plurality of solid electrolyte layers (the layers 1 to 6). However, the element body is not limited to this. The element body of the sensor element 101 may include at least one oxygen-ion-conductive solid electrolyte layer. For example, the layers 1 to 5 other than the second solid electrolyte layer 6 in FIG. 1 may be a layer formed of a material other than the solid electrolyte layer (e.g., layer formed of alumina). In this case, each electrode included in the sensor element 101 may be disposed on the second solid electrolyte layer 6. For example, the first measurement electrode 44 and the second measurement electrode 45 in FIG. 1 may be disposed on the lower surface of the second solid electrolyte layer 6. In addition, the reference-gas introduction space 43 may be provided in the spacer layer 5, not in the first solid electrolyte layer 4; the atmospheric-air introduction layer 48 may be provided between the second solid electrolyte layer 6 and the spacer layer 5, not between the first solid electrolyte layer 4 and the third substrate layer 3; and the reference electrode 42 may be provided backward of the third internal cavity 61 and on the lower surface of the second solid electrolyte layer 6.

In the above-described embodiment, the control unit 91 sets the target value V0* of the voltage V0 (performs feedback control) based on the pump current Ip1 such that the pump current Ip1 becomes the target value Ip1* and performs feedback control of the voltage Vp0 such that the voltage V0 becomes the target value V0*. However, the control unit 91 may perform another control. For example, the control unit 91 may perform feedback control of the voltage Vp0 based on the pump current Ip1 such that the pump current Ip1 becomes the target value Ip1*. That is, the control unit 91 may omit acquisition of the voltage V0 from the main-pump-controlling oxygen-partial-pressure detection sensor cell 80 and setting of the target value V0* and may directly control the voltage Vp0 (or control the pump current Ip0) based on the pump current Ip1.

In the above-described embodiment, the outer pump electrode 23 has roles of four electrodes, which are an outer main pump electrode to be a pair with the inner pump electrode 22 in the main pump cell 21, an outer auxiliary pump electrode to be a pair with the auxiliary pump electrode 51 in the auxiliary pump cell 50, the first outer measurement electrode to be a pair with the first measurement electrode 44 in the first measurement pump cell 41a, and the second outer measurement electrode to be a pair with the second measurement electrode 45 in the second measurement pump cell 41b. However, the outer pump electrode 23 is not limited to this. At least any one of the outer main pump electrode, the outer auxiliary pump electrode, the first outer measurement electrode, and the second outer measurement electrode may be provided outside the element body so as to contact with the measurement-object gas independently of the outer pump electrode 23. If the sensor element 101 includes three or more measurement pump cells, also, the outer pump electrode 23 may have all roles of the first to n-th outer measurement electrodes, and at least one of the first to n-th outer measurement electrodes may be provided outside the element body so as to contact with the measurement-object gas independently of the outer pump electrode 23.

Figure 15:
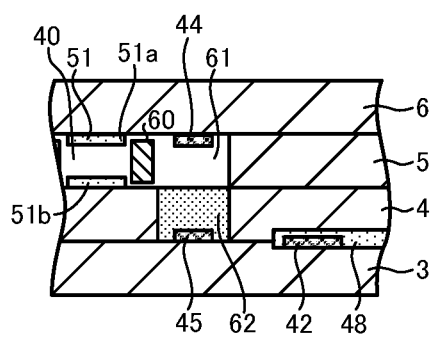
FIG. 15 is a schematic sectional view of the fifth diffusion-rate-controlling section 62 in a modification.

As another example of the embodiment illustrated in FIG. 9, that is, the embodiment in which the fourth diffusion-rate-controlling section 60 and the fifth diffusion-rate-controlling section 62 are arranged in a direction other than the front-to-back direction, and as another example of the embodiment in which a diffusion-rate-controlling section illustrated in FIGS. 10 to 13 is formed as a porous body, the embodiment illustrated in FIG. 15 can be given. In FIG. 15, the fifth diffusion-rate-controlling section 62 is disposed below the fourth diffusion-rate-controlling section 60 and the third internal cavity 61. The fifth diffusion-rate-controlling section 62 is formed as a porous body and is embedded in the first solid electrolyte layer 4 to vertically extend through the first solid electrolyte layer 4. The fifth diffusion-rate-controlling section 62 covers the second measurement electrode 45 disposed on the upper surface of the third substrate layer 3. The upper surface of the fifth diffusion-rate-controlling section 62 is exposed to the third internal cavity 61, and a flow line in the vertical direction from the third internal cavity 61 to the second measurement electrode 45 is formed. In FIG. 15, the fourth internal cavity 63 is not present, and the fifth diffusion-rate-controlling section 62 is located on a downstream side of the third internal cavity 61 and is embedded inside the element body. In the embodiment in FIG. 15, as in the embodiments in FIGS. 11 and 13, the inside of the fifth diffusion-rate-controlling section 62, that is, a portion around the second measurement electrode 45, serves as the second measurement chamber. In the embodiment in FIG. 15, also, the measurement-object gas flow section is configured such that the measurement-object gas passes through the first measurement-electrode diffusion-rate-controlling section (here, the fourth diffusion-rate-controlling section 60), the first measurement chamber (here, the third internal cavity 61), and the second measurement-electrode diffusion-rate-controlling section (here, the fifth diffusion-rate-controlling section 62) in this order and reaches the second measurement chamber. That is, the fourth diffusion-rate-controlling section 60 and the fifth diffusion-rate-controlling section 62 are disposed in series. Thus, as in the above-described embodiment, the second measurement pump cell 41b is suitable for detecting the NOx concentration that is higher than that in the first measurement pump cell 41a. Note that, in the example in FIG. 15, the fourth diffusion-rate-controlling section 60 is formed as two horizontally long slits as well as the third diffusion-rate-controlling section 30 in FIG. 1. However, the fourth diffusion-rate-controlling section 60 may be formed as a single horizontally long slit as well as the fourth diffusion-rate-controlling section 60 in FIG. 1. In addition, in FIG. 15, the second measurement electrode 45 is disposed on the upper surface of the third substrate layer 3, not on the upper surface of the first solid electrolyte layer 4, and thus, the positional relationship is preferably adjusted as appropriate so that the positions of the second measurement electrode 45 and the set of the reference electrode 42 and the atmospheric-air introduction layer 48 do not overlap with each other. In the example in FIG. 15, the set of the reference electrode 42 and the atmospheric-air introduction layer 48 is moved more backward than in the embodiment in FIG. 1 so as not to overlap with the second measurement electrode 45.

Figure 16:
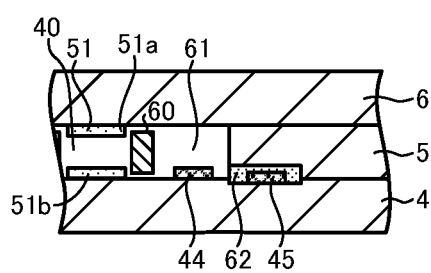
FIG. 16 is a schematic sectional view of the fifth diffusion-rate-controlling section 62 in a modification.

As another example of the embodiment in which a diffusion-rate-controlling section is formed as a porous body, the embodiment illustrated in FIG. 16 can also be given. In FIG. 16, the fifth diffusion-rate-controlling section 62 is formed as a porous body, and the fifth diffusion-rate-controlling section 62 covers the second measurement electrode 45. In FIG. 16, the fourth internal cavity 63 is not present, and the fifth diffusion-rate-controlling section 62 is located on a downstream side of the third internal cavity 61 and is sandwiched between the spacer layer 5 and the first solid electrolyte layer 4 and is embedded inside the element body. The front end of the fifth diffusion-rate-controlling section 62 is exposed to the third internal cavity 61. The second measurement electrode 45 is disposed on the upper surface of the first solid electrolyte layer 4 and is covered with the fifth diffusion-rate-controlling section 62. In the embodiment in FIG. 16, as in the embodiments in FIGS. 11 and 13, also, the inside of the fifth diffusion-rate-controlling section 62, that is, a portion around the second measurement electrode 45, serves as the second measurement chamber. In the case in FIG. 16, also, the fourth diffusion-rate-controlling section 60 and the fifth diffusion-rate-controlling section 62 are disposed in series. Thus, as in the above-described embodiment, the second measurement pump cell 41b is suitable for detecting the NOx concentration that is higher than that in the first measurement pump cell 41a. The diffusion resistance of the fifth diffusion-rate-controlling section 62 can be adjusted by adjusting, for example, each of the porosity, the pore size, the thickness (vertical length illustrated in FIG. 16), the width (horizontal length), and the length from an end on the upstream side to the second measurement electrode 45 (front-to-back length). The fifth diffusion-rate-controlling section 62 and the second measurement electrode 45 illustrated in FIG. 16 can be manufactured as follows, for example. On the upper surface of a ceramic green sheet corresponding to the first solid electrolyte layer 4, a paste for forming the fifth diffusion-rate-controlling section 62 and the second measurement electrode 45 is printed, and the ceramic green sheet and a ceramic green sheet corresponding to the spacer layer 5 are layered and fired.

In addition, the fifth diffusion-rate-controlling section 62 in FIG. 16 may be a slit-like gap instead of a porous body. For example, in the above manufacturing method, instead of the paste for forming the fifth diffusion-rate-controlling section 62 (porous body) in FIG. 16, if a paste of a vanishing material (e.g., theobromine) that vanishes by heating is printed, the paste vanishes by firing after layering the ceramic green sheets for forming the layers 1 to 6, and thereby, the portion of the fifth diffusion-rate-controlling section 62 in FIG. 16 can be formed as a slit-like gap (space) between the first solid electrolyte layer 4 and the spacer layer 5. If the portion of the fifth diffusion-rate-controlling section 62 in FIG. 16 is formed as a slit-like gap, in the fifth diffusion-rate-controlling section 62, in particular, a portion from an end on an upstream side (i.e., the front end) of the fifth diffusion-rate-controlling section 62 to the front end of the second measurement electrode 45 corresponds to the second measurement-electrode diffusion-rate-controlling section. In addition, a gap (space) around the second measurement electrode 45 in the fifth diffusion-rate-controlling section 62 corresponds to the second measurement chamber. If the fifth diffusion-rate-controlling section 62 is a slit-like gap, the diffusion resistance of the fifth diffusion-rate-controlling section 62 can be adjusted by adjusting, for example, at least any of the thickness, the width, and the length from the end on the upstream side to the second measurement electrode 45 of the fifth diffusion-rate-controlling section 62.

Figure 17:
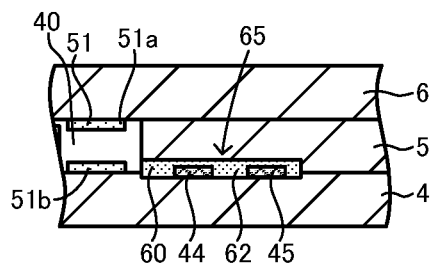
FIG. 17 is a schematic sectional view of the fourth diffusion-rate-controlling section 60 and the fifth diffusion-rate-controlling section 62 in a modification.

The embodiment in FIG. 16 may be configured as in FIG. 17 by changing to form, not only the fifth diffusion-rate-controlling section 62, but also the fourth diffusion-rate-controlling section 60 as a porous body. In FIG. 17, a route of the measurement-object gas from the second internal cavity 40 to the second measurement electrode 45 is formed of a porous body 65. The porous body 65 is disposed to be sandwiched between the first solid electrolyte layer 4 and the spacer layer 5 and embedded inside the element body. The porous body 65 covers the first measurement electrode 44 and the second measurement electrode 45 disposed on the upper surface of the first solid electrolyte layer 4. In FIG. 17, a portion of the porous body 65 from the front end to the first measurement electrode 44 is the fourth diffusion-rate-controlling section 60, and a portion of the porous body 65 between the first measurement electrode 44 and the second measurement electrode 45 is the fifth diffusion-rate-controlling section 62. In addition, a portion between the porous body 65 and the first measurement electrode 44, in other words, a portion around the first measurement electrode 44, serves as the first measurement chamber. Similarly, a portion between the porous body 65 and the second measurement electrode 45 serves as the second measurement chamber. In the embodiment in FIG. 17, also, the fourth diffusion-rate-controlling section 60 and the fifth diffusion-rate-controlling section 62 are disposed in series. Thus, as in the above-described embodiment, the second measurement pump cell 41*b* is suitable for detecting the NOx concentration that is higher than that in the first measurement pump cell 41*a*. The porous body 65, the first measurement electrode 44, and the second measurement electrode 45 in FIG. 17 can be manufactured by substantially the same method as that for the fifth diffusion-rate-controlling section 62 and the second measurement electrode 45 in FIG. 16. In FIG. 17, also, the portion of the porous body 65 may be a slit-like gap instead of a porous body.

What is claimed is:

1. A gas sensor comprising a sensor element for detecting a concentration of a specific gas in a measurement-object gas, the gas sensor comprising:

an element body including an oxygen-ion-conductive solid electrolyte layer and having a measurement-object gas flow section provided therein, the measurement-object gas flow section introducing the measurement-object gas and causing the measurement-object gas to flow;

an adjustment pump cell that adjusts an oxygen concentration in an oxygen concentration adjustment chamber in the measurement-object gas flow section;

a first measurement pump cell that includes a first measurement electrode and a first outer measurement electrode and that pumps out oxygen produced in a first measurement chamber from the specific gas, the first measurement electrode being disposed in the first measurement chamber provided on a downstream side of the oxygen concentration adjustment chamber in the measurement-object gas flow section, the first outer measurement electrode being provided outside the element body so as to contact with the measurement-object gas;

a second measurement pump cell that includes a second measurement electrode and a second outer measurement electrode and that pumps out oxygen produced in a second measurement chamber from the specific gas, the second measurement electrode being disposed in the second measurement chamber provided on the downstream side of the oxygen concentration adjustment chamber in the measurement-object gas flow section, the second outer measurement electrode being provided outside the element body so as to contact with the measurement-object gas, and a specific gas concentration detection device having a low concentration measurement mode and a high concentration measurement mode, the low concentration measurement mode being a mode on which the first measurement pump cell is controlled such that a pump current that flows in the first measurement pump cell becomes a limiting current, and, based on a value of the pump current, the specific gas concentration in the measurement-object gas is detected, the high concentration measurement mode being a mode on which the second measurement pump cell is controlled such that a pump current that flows in the second measurement pump cell becomes a limiting current, and, based on a value of the pump current, the specific gas concentration in the measurement-object gas is detected, wherein the measurement-object gas flow section is configured such that the measurement-object gas passes through the oxygen concentration adjustment chamber and a first measurement-electrode diffusion-rate-controlling section in this order and reaches the first measurement chamber and that the measurement-object gas passes through the first measurement chamber and a second measurement-electrode diffusion-rate-controlling section in this order and reaches the second measurement chamber.

2. The gas sensor according to claim 1,
wherein the first measurement-electrode diffusion-rate-controlling section is a slit-like gap or a porous body, and
wherein the second measurement-electrode diffusion-rate-controlling section is a slit-like gap or a porous body.

3. The gas sensor according to claim 1, further comprising:
when n is an integer of greater than or equal to 3, first to n-th measurement pump cells including the first measurement pump cell and the second measurement pump cell,
wherein, when p is an integer from 3 to n, a p-th measurement pump cell includes a p-th measurement electrode and a p-th outer measurement electrode and is configured to pump out oxygen produced in a p-th measurement chamber from the specific gas, the p-th measurement electrode being disposed in the p-th measurement chamber provided on the downstream side of the oxygen concentration adjustment chamber in the measurement-object gas flow section, the p-th outer measurement electrode being provided outside the element body so as to contact with the measurement-object gas, and
wherein the measurement-object gas flow section is configured such that the measurement-object gas passes through a (p−1)-th measurement chamber and a p-th measurement-electrode diffusion-rate-controlling section in this order and reaches the p-th measurement chamber.

4. The gas sensor according to claim 3,
wherein, when k is an integer from 1 to n−1, a ratio $R_{k+1}/R_k$ between a k-th diffusion resistance $R_k$ and a (k+1)-th diffusion resistance $R_{k+1}$ is greater than 1 and less than or equal to 100, the k-th diffusion resistance $R_k$ being a diffusion resistance of a route of the measurement-object gas from an outside to a k-th measurement electrode, the (k+1)-th diffusion resistance $R_{k+1}$ being a diffusion resistance of a route of the measurement-object gas from the outside to a (k+1)-th measurement electrode.

5. The gas sensor according to claim 1,
wherein, if the specific gas concentration detection device determines, based on the pump current that flows in the first measurement pump cell on the low concentration measurement mode, that the specific gas concentration in the measurement-object gas is included in a predetermined high concentration region, the specific gas concentration detection device switches to the high concentration measurement mode, and, if the specific gas concentration detection device determines, based on the pump current that flows in the second measurement pump cell on the high concentration measurement mode, that the specific gas concentration in the measurement-object gas is included in a predetermined low concentration region, the specific gas concentration detection device switches to the low concentration measurement mode.

6. A gas sensor for detecting an oxygen concentration as a concentration of a specific gas in a measurement-object gas, the gas sensor comprising:
an element body including an oxygen-ion-conductive solid electrolyte layer and having a measurement-object gas flow section provided therein, the measurement-object gas flow section introducing the measurement-object gas and causing the measurement-object gas to flow;
a first measurement pump cell that includes a first measurement electrode and a first outer measurement electrode and that pumps out oxygen in the measurement-object gas, the first measurement electrode being disposed in a first measurement chamber in the measurement-object gas flow section, the first outer measurement electrode being provided outside the element body so as to contact with the measurement-object gas; and
a second measurement pump cell that includes a second measurement electrode and a second outer measurement electrode and that pumps out oxygen in the measurement-object gas, the second measurement electrode being disposed in a second measurement chamber in the measurement-object gas flow section, the second outer measurement electrode being provided outside the element body so as to contact with the measurement-object gas, and
a specific gas concentration detection device having a low concentration measurement mode and a high concentration measurement mode, the low concentration measurement mode being a mode on which the first measurement pump cell is controlled such that a pump current that flows in the first measurement pump cell becomes a limiting current, and, based on a value of the pump current, the specific gas concentration in the measurement-object gas is detected, the high concentration measurement mode being a mode on which the second measurement pump cell is controlled such that a pump current that flows in the second measurement pump cell becomes a limiting current, and, based on a value of the pump current, the specific gas concentration in the measurement-object gas is detected,
wherein the measurement-object gas flow section is configured such that the measurement-object gas passes through a first measurement-electrode diffusion-rate-controlling section and reaches the first measurement chamber and that the measurement-object gas passes through the first measurement chamber and a second measurement-electrode diffusion-rate-controlling section in this order and reaches the second measurement chamber.

* * * * *